US012676083B2

(12) United States Patent
Paull et al.

(10) Patent No.: US 12,676,083 B2
(45) Date of Patent: Jul. 7, 2026

(54) ULTRASOUND SIMULATION

(71) Applicant: VANTARI PTY LTD, West Pennant Hills (AU)

(72) Inventors: Daniel Loyd Paull, West Pennant Hills (AU); Vijaynath Pereembarajah Paul, West Pennant Hills (AU); Nishanth Krishnananthan, West Pennant Hills (AU)

(73) Assignee: VANTARI PTY LTD, West Pennant Hills (AU)

( * ) Notice: Subject to any disclaimer, the term of this patent is extended or adjusted under 35 U.S.C. 154(b) by 0 days.

(21) Appl. No.: 18/579,002

(22) PCT Filed: Jul. 15, 2022

(86) PCT No.: PCT/AU2022/050746
§ 371 (c)(1),
(2) Date: Jan. 12, 2024

(87) PCT Pub. No.: WO2023/283695
PCT Pub. Date: Jan. 19, 2023

(65) Prior Publication Data
US 2024/0339046 A1      Oct. 10, 2024

(30) Foreign Application Priority Data
Jul. 16, 2021    (AU) ................................. 2021902193

(51) Int. Cl.
*A61B 34/10*          (2016.01)
*G06T 15/08*          (2011.01)
(Continued)

(52) U.S. Cl.
CPC ............ *G09B 23/286* (2013.01); *A61B 34/10* (2016.02); *G06T 15/08* (2013.01); *G06T 19/20* (2013.01);
(Continued)

(58) Field of Classification Search
CPC ........ G09B 23/286; G09B 9/00; A61B 34/10; A61B 2034/102; A61B 2034/2063;
(Continued)

(56) References Cited

U.S. PATENT DOCUMENTS

| | | | |
|---|---|---|---|
| 6,069,634 A * | 5/2000 | Gibson | ................... G06T 19/20 |
| | | | 345/424 |
| 8,480,404 B2 | 7/2013 | Savitsky | |
(Continued)

FOREIGN PATENT DOCUMENTS

| | | |
|---|---|---|
| CN | 102496320 A | 6/2012 |
| WO | WO-2007100263 A1 | 9/2007 |
(Continued)

OTHER PUBLICATIONS

Burger, B. et al., 'Real-time GPU-based ultrasound simulation using deformable mesh models', IEEE Transactions on Medical Imaging, 2013, vol. 32, No. 3, pp. 609-618.
(Continued)

*Primary Examiner* — Eddy Saint-Vil
(74) *Attorney, Agent, or Firm* — Mintz Levin Cohn Ferris Glovsky and Popeo PC

(57) ABSTRACT

Disclosed is a method of simulating an ultrasound scan of tissue in real-time. The method comprises loading a three dimensional deformable soft tissue model of a tissue region for scanning, the deformable soft tissue model being a volumetric model and determining a three dimensional interaction between the deformable soft tissue model and at least one medical tool. The method also comprises modifying the deformable soft tissue model according to the three dimensional interaction and properties of the deformable soft tissue model, the properties including compressible and incompressible regions of the deformable soft tissue model and generating a simulated scan of the tissue in real-time
(Continued)

according to a position of an ultrasound probe and the modified soft tissue model.

16 Claims, 15 Drawing Sheets

(51) Int. Cl.

| | |
|---|---|
| *G06T 19/20* | (2011.01) |
| *G09B 9/00* | (2006.01) |
| *G09B 23/28* | (2006.01) |
| *A61B 34/20* | (2016.01) |

(52) U.S. Cl.
CPC .......... *G09B 9/00* (2013.01); *A61B 2034/102* (2016.02); *A61B 2034/2063* (2016.02); *G06T 2210/41* (2013.01); *G06T 2210/56* (2013.01); *G06T 2219/2021* (2013.01)

(58) Field of Classification Search
CPC ........ A61B 2034/104; A61B 2034/105; A61B 2090/378; A61B 34/25; A61B 2034/101; A61B 2034/107; A61B 2034/252; A61B 2090/365; G06T 15/08; G06T 19/20; G06T 2210/41; G06T 2210/56; G06T 2219/2021; G06T 15/00; G16H 40/63; G16H 40/67; G16H 50/50
See application file for complete search history.

(56) References Cited

U.S. PATENT DOCUMENTS

| | | | | |
|---|---|---|---|---|
| 9,626,805 | B2 | 4/2017 | Lampotang et al. | |
| 10,565,900 | B2 | 2/2020 | Mattausch et al. | |
| 2005/0010326 | A1* | 1/2005 | Hayward ................ | G06F 30/23 700/182 |
| 2007/0008317 | A1* | 1/2007 | Lundstrom ............. | G06T 15/08 345/424 |
| 2010/0104162 | A1 | 4/2010 | Falk et al. | |
| 2013/0323700 | A1* | 12/2013 | Samosky ............... | G09B 23/30 434/262 |
| 2014/0272866 | A1* | 9/2014 | Kim ....................... | G09B 23/28 434/262 |
| 2016/0022369 | A1* | 1/2016 | Audigier ................ | G09B 23/30 434/268 |
| 2016/0328998 | A1* | 11/2016 | Pedersen .............. | G09B 23/286 |
| 2017/0352294 | A1* | 12/2017 | Nataneli .............. | G09B 23/286 |
| 2020/0005550 | A1* | 1/2020 | Schneider .............. | G06T 19/20 |
| 2020/0250892 | A1* | 8/2020 | O'Brien .................. | G06T 17/10 |
| 2021/0166478 | A1* | 6/2021 | Pai .......................... | G06T 17/20 |
| 2022/0000566 | A1* | 1/2022 | Regensburger ........ | A61B 34/10 |
| 2023/0061175 | A1* | 3/2023 | Shivashankar ......... | G06F 3/011 |
| 2024/0157559 | A1* | 5/2024 | Liu ......................... | A61B 34/30 |

FOREIGN PATENT DOCUMENTS

| | | |
|---|---|---|
| WO | WO-2010034117 A1 | 4/2010 |
| WO | WO-2016149805 A1 | 9/2016 |
| WO | WO-2017064249 A1 | 4/2017 |
| WO | WO-2018035310 A1 | 2/2018 |

OTHER PUBLICATIONS

Camara, M. et al., 'Simulation of patient-specific deformable ultrasound imaging in real time', BIVPCS/POCUS 2017, Lecture Notes in Computer Science, 2017, vol. 10549, pp. 11-18.

Charles Barnouin, Florence Zara, Fabrice Jaillet. A real-time ultrasound rendering with model-based tissue deformation for needle insertion. 15th International Conference on Computer Graphics Theory and Applications, GRAPP 2020, Feb. 2020, Valletta, Malta. ff10.5220/0008947302350246ff. ffhal 02415740.

European Search Report for European Patent Application No. 22840873.8 dated Oct. 4, 2025 (9 pages).

K. Petrinec, "Patient-Specific Interactive Ultrasound Image Simulation with Soft-Tissue Deformation," University of California, Los Angeles, USA, 2013.

CAE Healthcare, "CAE Vimedix 3.0 ultrasound simulator," uploaded Jan. 17, 2020, video available from <https://vimeo.com/385484066>.

CAE Healthcare, "CAE Vimedix ultrasound simulator," uploaded Apr. 29, 2020, video available from <https://vimeo.com/413237073>.

CAE Healthcare, "CAE VimedixAR Preview," uploaded May 20, 2020, video available from <https://vimeo.com/420817738>.

CAE Vimedix, "Ultrasound Simulatoin," dated 2024, copy downloaded Jan. 10, 2024, available from <https://www.caehealthcare.com/solutions/brands/cae-vimedix/>.

Camara, M. et al., 'Soft tissue deformation for surgical simulation: a position-based dynamics approach', Int J Cars, 2016, vol. 11, pp. 919-928.

Cong W, Yang J, Liu Y, Wang Y. "Fast and automatic ultrasound simulation from CT images" Comput Math Methods Med. 2013;2013:327613. doi: 10.1155/2013/327613. Epub Nov. 18, 2013. PMID: 24348736; PMCID:PMC3855946.

Eleonora Tagliabue, Diego Dall'alba, Enrico Magnabosco, Chiara Tenga, Igor Peterlik, et al. "Position-based modeling of lesion displacement in Ultrasound-guided breast biopsy" International Journal of Computer Assisted Radiology and Surgery, 2019, 14 (8), pp. 1329-1339. ?10.1007/s11548-019-01997-z?. ?hal-02276090?

Goksel O, Salcudean SE. B-mode ultrasound image simulation in deformable 3-D medium. IEEE Trans Med Imaging. Nov. 2009;28(11):1657-69. doi: 10.1109/TMI.2009.2016561. Epub Mar. 10, 2009. PMID: 19278928.

Goksel O, Salcudean SE. Fast B-mode ultrasound image simulation of deformed tissue. Annu Int Conf IEEE Eng Med Biol Soc. 2007;2007:87-90. doi: 10.1109/IEMBS.2007.4352229. PMID:18001895.

HealthySimulation—Medical Simulatoin Resources, "SonoSim Ultrasound Simulator Demo at IMSH 2020," uploaded Mar. 5, 2020, video available from <https://www.youtube.com/watch?v=gnJlwqEydTA&feature=youtu.be>.

HealthySimulatoin—Medical Simulatoin Resources, "Medaphor Ultrasound Simulator Training | HealthySimulation.com Interview," uploaded Aug. 13, 2014, video available from <https://www.youtube.com/watch?v=DutMsawgwu8>.

I. Berndt, R. Torchelsen and A. Maciel, "Efficient Surgical Cutting with Position-Based Dynamics" in IEEE Computer Graphics and Applications, vol. 37, No. 03, pp. 24-31, 2017. doi:10.1109/MCG.2017.45.

Intelligent Ultrasound, "Introducing BodyWorks Eve Point of Care Ultrasound Simulation," uploaded Feb. 26, 2019, video available from <https://www.youtube.com/watch?v=MWuAVUKV29k>.

K. Petrinec, E. Savitsky and D. Terzopoulos, "Patient-Specific Interactive Simulation of Compression Ultrasonography," 2014 IEEE 27th International Symposium on Computer-Based Medical Systems, New York, NY, USA, 2014, pp. 113-118, doi:10.1109/CBMS.2014.76.

M. Macklin, K. Storey, M. Lu, P. Terdiman, N. Chentanez, S. Jeschke, M. Müller—"Small Steps in Physics Simulation" Symposium on Computer Animation (SCA 2019).

M. Macklin, M. Müller, N. Chentanez—"XPBD: Position-Based Simulation of Compliant Constrained Dynamics" Motion in Games (2016).

M. Müller, B. Heidelberger, M. Hennix, J. Ratcliff "Position Based Dynamics" Virtual Reality Interactions and Physical Simulations (VRIPhys) 2006.

M. Müller, N. Chentanez, T.Y. Kim, M. Macklin "Air Meshes for Robust Collision Handling" ACM Transactions on Graphics (SIGGRAPH 2015).

Miles Macklin, "XPBD slides and stiffness," Oct. 12, 2016, available from <http://blog.mmacklin.com/2016/10/12/xpbd-slides-and-stiffness/>.

(56) References Cited

OTHER PUBLICATIONS

O. Mattausch, O. Goksel. "Monte-Carlo ray-tracing for realistic interactive ultrasound simulation." VCBM '16: Proceedings of the Eurographics Workshop on Visual Computing for Biology and Medicine.

Østergaard ML, Konge L, Kahr N, Albrecht-Beste E, Nielsen MB, Nielsen KR. Four Virtual-Reality Simulators for Diagnostic Abdominal Ultrasound Training in Radiology. Diagnostics (Basel). May 6, 2019;9(2):50. doi: 10.3390/diagnostics9020050. PMID: 31064080; PMCID:PMC6627565.

Pepley DF, Adhikary SD, Miller SR, Moore JZ. Simulating Ultrasound Tissue Deformation Using Inverse Mapping. J Comput Nonlinear Dyn. Oct. 1, 2019;14(10):101004-1010048. doi:10.1115/1.4042809. Epub Sep. 9, 2019. PMID: 32280313; PMCID: PMC7104777.

Romeo, M., Monteagudo, C. and Sánchez-Quirós, D. (2020), Muscle and Fascia Simulation with Extended Position Based Dynamics. Computer Graphics Forum, 39: 134-146. https://doi.org/10.1111/cgf.13734.

Schallware, "Description of Schallware Ultrasound Simulator," copy downloaded Jan. 10, 2024, available from <https://www.schallware.de/en/description>.

Sonosim, "Internal Jugular Vein Cannulatoin Ultrasound-Guided Procedure Training," copy downloaded Jan. 10, 2024, available from <https://store.sonosim.com/ultrasound-guided-internal-jugular-vein-cannulation-procedure-training/>.

Sonosim, "The Easiest Way to Learn & Teach Ultrasonography® ", dated 2023, available from <https://sonosim.com/>.

Sonosim, "Ultrasound-Guided Procedures," dated 2023, available from <https://sonosim.com/ultrasound-procedure-practice-simulator>.

Surgical Science, "U/S Mentor in the 1st Israeli Palestinian POCUS collaborative course," uploaded May 28, 2018, video available from <https://vimeo.com/272164032>.

Surgical Science, uploaded May 16, 2018, "U/S VR Task" video available from <https://vimeo.com/270066722>.

Surgicalscience, "Ultrasound Mentor: One Platform for All Your Ultrasound Training Needs," copy downloaded Jan. 10, 2024, available from <https://surgicalscience.com/simulators/u-s-mentor/>.

Surgicalscience, "VR Add-On for Ultrasound Mentor," copy downloaded Jan. 10, 2024, available from <https://surgicalscience.com/simulators/u-s-mentor/vr-add-on/>.

Teresa Gore, "Intelligent Ultrasound for smarter scanning," dated Dec. 18, 2023, available from <https://www.healthysimulation.com/medical-simulation/vendors/intelligent-ultrasound/>.

Teresa Gore, "Ultrasound Simulator," dated Dec. 18, 2023, available from <https://www.healthysimulation.com/ultrasound-simulator/>.

* cited by examiner

500

ULTRASOUND SIMULATION

CROSS-REFERENCE TO RELATED APPLICATIONS

The present application claims priority to and is the 35 U.S.C. 371 United States National Phase application based on International Patent Application No. PCT/AU2022/050746, filed on Jul. 15, 2022, entitled "ULTRASOUND SIMULATION," which claims priority to Australian Patent Application No. 2021902193 filed Jul. 16, 2021, which are hereby incorporated by reference in their entireties.

TECHNICAL FIELD

The present invention relates to ultrasound simulation, and particularly to ultrasound simulation including a medical tool.

BACKGROUND

Ultrasounds machines are commonly used in a range of medical procedures for both diagnosis and clinical practice. For diagnosis they are used as a diagnostic imaging modality. In clinical practice, the "gold standard" is to use ultrasound in an increasing number of medical procedures. Some examples include the use of ultrasound sonography either for point of care ultrasound (POCUS) and focused assessment with sonography for trauma (FAST), or for assisting a surgeon for part of an ultrasound guided surgical procedure.

The increasing use of medical procedures involving ultrasound has resulted in a need for ultrasound training to extend beyond traditional training approaches. One existing approach for ultrasound training is the use of a training mannequin. Mannequins cannot be easily adapted to different scenarios, especially simulating pathological cases. Mannequin based systems that use a real ultrasound machine allow for the teaching of ultrasound techniques, but require both a mannequin and an ultrasound machine, compounding the expense of the system. As a result, such training may be expensive and resource intensive. For example, with a mannequin based system it may be difficult to show patient specific data. The training may also be limited by the mannequin and use of a predetermined model. For example, it may be difficult to present patients of different body shape, age, gender, etc. other than by providing a mannequin for each permutation of such characteristics. Using an ultrasound machine may require ultrasound machines for training only purposes or may remove ultrasound machines from being used for diagnostic purposes. The result is that additional cost is either spent on purchasing and maintaining ultrasound machines or ultrasound machine availability decreases for diagnostic purposes while providing limited training benefits. Also, clinicians are increasingly having to travel or attend workshops over many days for access to ultrasound and POCUS training. Clinicians also have to review and retain proficiency over time by repeating such expenses or workshops. Foundational training, upskilling, access to training and deskilling are all considerations of the modern clinician with regards to ultrasound which has profound implications for patient safety and outcomes.

An alternative approach to ultrasound training has been to use an ultrasound simulator. In one system, ultrasound images may be recorded from patients. The recorded ultrasound images are used to generate an ultrasound image in a simulator. As an operator moves a physical ultrasound probe, the ultrasound simulator may modify the recorded ultrasound image or images to show the effect of moving the ultrasound probe on a patient. However, such approaches may result in behaviour that does not accurately model the behaviour of an ultrasound when used on a patient as the modification of the recorded ultrasound scan images may lack accuracy and not be a true representation of a real ultrasound image of a patient. Further, such approaches may not be able to produce an accurate representation for an ultrasound guided surgical procedure. Ultrasound simulators are also restrictive and narrow in their "scope" of training and practice. From a technology perspective ultrasound simulators don't have the advantage of being adaptive or real-time while from a clinical perspective ultrasound simulators are limited and lack breadth and depth of training delivery.

SUMMARY

One embodiment includes a method of simulating an ultrasound scan of tissue in real-time, the method comprising: loading a three dimensional deformable soft tissue model of a tissue region for scanning, the deformable soft tissue model being a volumetric model; determining a three dimensional interaction between the deformable soft tissue model and at least one medical tool; modifying the deformable soft tissue model according to the three dimensional interaction and properties of the deformable soft tissue model, the properties including compressible and incompressible regions of the deformable soft tissue model; and generating a simulated scan of the tissue in real-time according to a position of an ultrasound probe and the modified soft tissue model.

In one embodiment, the deformable soft tissue model includes a plurality of particles and each of the plurality of particles are linked using at least one constraint.

In one embodiment, the deformable soft tissue model comprises a mesh and each of the plurality of particles are located at vertices of the mesh.

In one embodiment, a first particle of the plurality of particles is linked to a second particle of the plurality of particles of the deformable soft tissue model using at least one constraint.

In one embodiment, the at least one constraint is selected from the set consisting of a distance constraint, a volume constraint and a contact constraint.

In one embodiment, particles in a compressible region of the deformable soft tissue model are connected to adjacent particles with distance constraints and particle in an incompressible region of the deformable soft tissue model are connected to adjacent particles with volume constraints.

In one embodiment, a voxel model overlaps the deformable soft tissue model and is used to derive continuously varying material properties of the deformable soft tissue model.

In one embodiment, the voxel model has a resolution different to the deformable soft tissue model.

In one embodiment, a model of the medical tool includes a plurality of particles and a particle of the plurality of particles is linked to a particle of the plurality of particles of the deformable soft tissue model using at least one constraint.

In one embodiment, modifying the deformable soft tissue model comprises: locating particles of the deformable soft tissue model nearby the medical tool; attaching a plurality of particles of the deformable soft tissue model to a plurality of particles of the medical tool using constraints; and determining a new location for the plurality of particles of the deformable soft tissue model and a new location for the plurality of particles of the medical tool base on movement of the medical tool.

In one embodiment, the at least one constraint is selected from the set consisting of a distance constraint, a volume constraint and a contact constraint.

In one embodiment, the medical tool is selected from a set of medical tools consisting of an ultrasound probe, a hypodermic needle, a cannula, a scalpel, sutures, dressing, and forceps.

In one embodiment, the deformable soft tissue model is formed from a scan selected from the set of a CT scan and a MRI scan.

In one embodiment, the modification to the deformable soft tissue model is performed by a position based dynamics solver.

In one embodiment, the position based dynamics solver is a Small Steps approach to an extended position based dynamics (XPBD) solver.

In one embodiment, generating the simulated scan further comprises: forming an image slice using material properties of the medical tool and the properties of the deformable soft tissue model, wherein the material properties of the medical tool produce acoustic anomalies associated with the medical tool.

One embodiment includes a virtual ultrasound system for simulating an ultrasound scan of tissue in real-time, the system comprising: a deformable soft tissue model of a tissue region, the deformable soft tissue model being a volumetric model; a model of at least one medical tool; a position based dynamics solver configured to determine a three dimensional interaction between the deformable soft tissue model and the model of the at least one medical tool in real-time, the position based dynamics solver also being configured to modify the deformable soft tissue model according to the three dimensional interaction and properties of the deformable soft tissue model, wherein the properties include compressible and incompressible regions of the deformable soft tissue model; an acoustic simulator configured to generate a simulated scan of the tissue according to a position of an ultrasound probe and the modified soft tissue model; and an output device for displaying the simulated scan of the tissue.

In one embodiment, the deformable soft tissue model includes a plurality of particles and each of the plurality of particles are linked using at least one constraint.

In one embodiment, the deformable soft tissue model comprises a mesh and each of the plurality of particles are located at a vertices of the mesh.

In one embodiment, a first particle of the plurality of particles is linked to a second particle of the plurality of particles of the deformable soft tissue model using at least one constraint.

In one embodiment, the at least one constraint is selected from the set consisting of a distance constraint, a volume constraint and a contact constraint.

In one embodiment, particles in a compressible region of the deformable soft tissue model are connected to adjacent particles with distance constraints and particle in an incompressible region of the deformable soft tissue model are connected to adjacent particles with volume constraints.

In one embodiment, a voxel model overlaps the deformable soft tissue model and is used to derive continuously varying material properties of the deformable soft tissue model.

In one embodiment, the voxel model has a resolution different to the deformable soft tissue model.

In one embodiment, a model of the medical tool includes a plurality of particles and a particle of the plurality of particles of the model of the medical tool is linked to a particle of the plurality of particles of the deformable soft tissue model using at least one constraint.

In one embodiment, the at least one constraint is selected from the set consisting of a distance constraint, a volume constraint and a contact constraint.

In one embodiment, the medical tool is selected from a set of medical tools consisting of an ultrasound probe, a hypodermic needle, a cannula, a scalpel, sutures, dressing, and forceps.

In one embodiment, the deformable soft tissue model is formed from a scan selected from the set of a CT scan and a MRI scan.

In one embodiment, the position based dynamics solver is an extended position based dynamics (XPBD) solver.

In one embodiment, the position based dynamics solver is a Small Steps approach to an extended position based dynamics (XPBD) solver.

In one embodiment, the acoustic simulator further comprises: an image slice generator configured to form an image slice using material properties of the medical tool and the properties of the deformable soft tissue model, wherein material properties of the medical tool produce acoustic anomalies associated with the medical tool.

BRIEF DESCRIPTION OF FIGURES

At least one embodiment of the present invention is described, by way of example only, with reference to the accompanying figures.

DETAILED DESCRIPTION

Disclosed is method of simulating an ultrasound scan of tissue. The method may comprise loading a three dimensional soft tissue model of a tissue region for scanning. A three dimensional interaction between the soft tissue model and at least one medical tool may be determined. Next, the soft tissue model may be modified according to the three dimensional interaction and properties of the soft tissue model. The properties may include compressible and incompressible regions of the soft tissue model. A simulated scan of the tissue may be generated according to a position of an ultrasound probe and the modified soft tissue model.

A dynamic virtual ultrasound simulates imaging and user interactions required to perform diagnostic ultrasound imaging and ultrasound guided procedures. The dynamic virtual ultrasound includes a soft tissue model, also referred to as a deformable soft tissue model, a volumetric soft tissue model or a soft body dynamics soft tissue model which is a soft tissue model simulated using soft body dynamics. The soft tissue model implements tissue mechanics so that soft tissue may be deformed by external influences, such as gravity, applied pressure, medical tools and pressure inside vessels. The soft tissue model is a model of the soft tissue, bones, joints, organs, etc. of the patient using soft body dynamics.

The dynamic virtual ultrasound also includes various modelled medical tools that may interact with and deform the soft tissue model. Also included is a position based dynamics solver for the soft tissue model and interaction between the modelled medical tools and the soft tissue model. The position based dynamics solver may also be referred to as a soft body dynamics solver. An acoustic simulator may also form part of the dynamic virtual ultrasound. The acoustic simulator may be based on a model of a medical ultrasound machine including machine settings, transducer characteristics, soft tissue response and acoustic anomalies. The acoustic simulation may include anomalies found in real ultrasound imaging such as anomalies related to the use of surgical implements, e.g. comet-tails from needle tips. The dynamic virtual ultrasound also has a user interface that may receive user inputs and provide feedback in both visual and haptic forms to the user. As part of the user interface the internal parts of the soft tissue model of a patient may be visualised through the use of a virtual ultrasound probe, as would be used for diagnostic sonography or in ultrasound guided surgical procedures.

Figure 1:
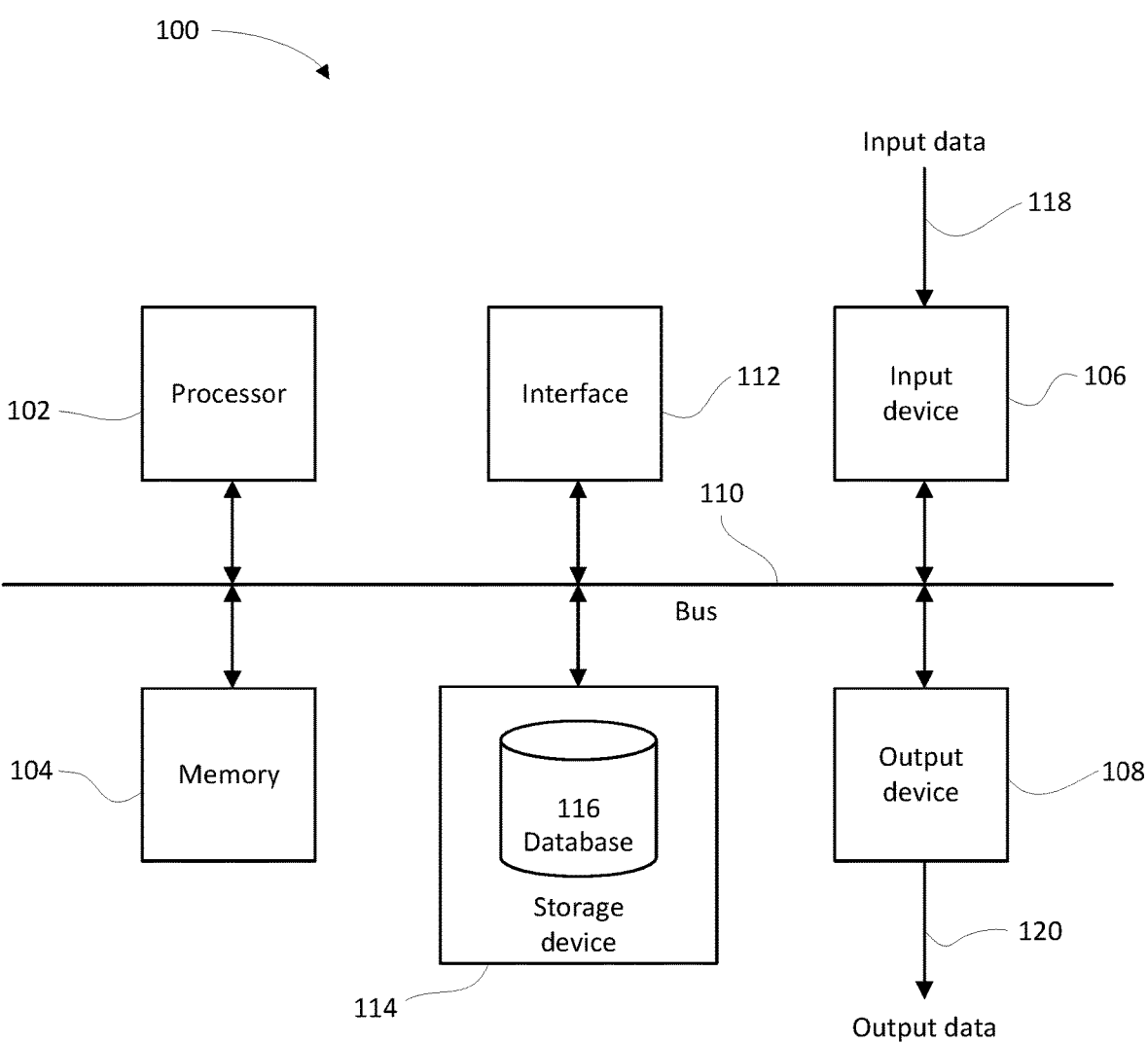
FIG. 1 illustrates a functional block diagram of an example processing system that can be utilised to embody or give effect to a particular embodiment.

A particular embodiment of the present invention can be realised using a processing system, an example of which is shown in FIG. 1. In particular, the processing system 100 generally includes at least one processor 102, or processing unit or plurality of processors, memory 104, at least one input device 106 and at least one output device 108, coupled together via a bus or group of buses 110. In certain embodiments, input device 106 and output device 108 could be the same device. An interface 112 can also be provided for coupling the processing system 100 to one or more peripheral devices, for example interface 112 could be a PCI card or PC card. At least one storage device 114 which houses at least one database 116 can also be provided. The memory 104 can be any form of memory device, for example, volatile or non-volatile memory, solid state storage devices, magnetic devices, etc. The processor 102 could include more than one distinct processing device, for example to handle different functions within the processing system 100.

Input device 106 receives input data 118 and can include, for example, a keyboard, a pointer device such as a pen-like device or a mouse, audio receiving device for voice controlled activation such as a microphone, data receiver or antenna such as a modem or wireless data adaptor, data acquisition card, etc. Input data 118 could come from different sources, for example keyboard instructions in conjunction with data received via a network. Output device 108 produces or generates output data 120 and can include, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 could be distinct and derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, etc.

In use, the processing system 100 is adapted to allow data or information to be stored in and/or retrieved from, via wired or wireless communication means, the at least one database 116. The interface 112 may allow wired and/or wireless communication between the processing unit 102 and peripheral components that may serve a specialised purpose. The processor 102 receives instructions as input data 118 via input device 106 and can display processed results or other output to a user by utilising output device 108. More than one input device 106 and/or output device 108 can be provided. It should be appreciated that the processing system 100 may be any form of terminal, server, specialised hardware, or the like.

Figure 2:
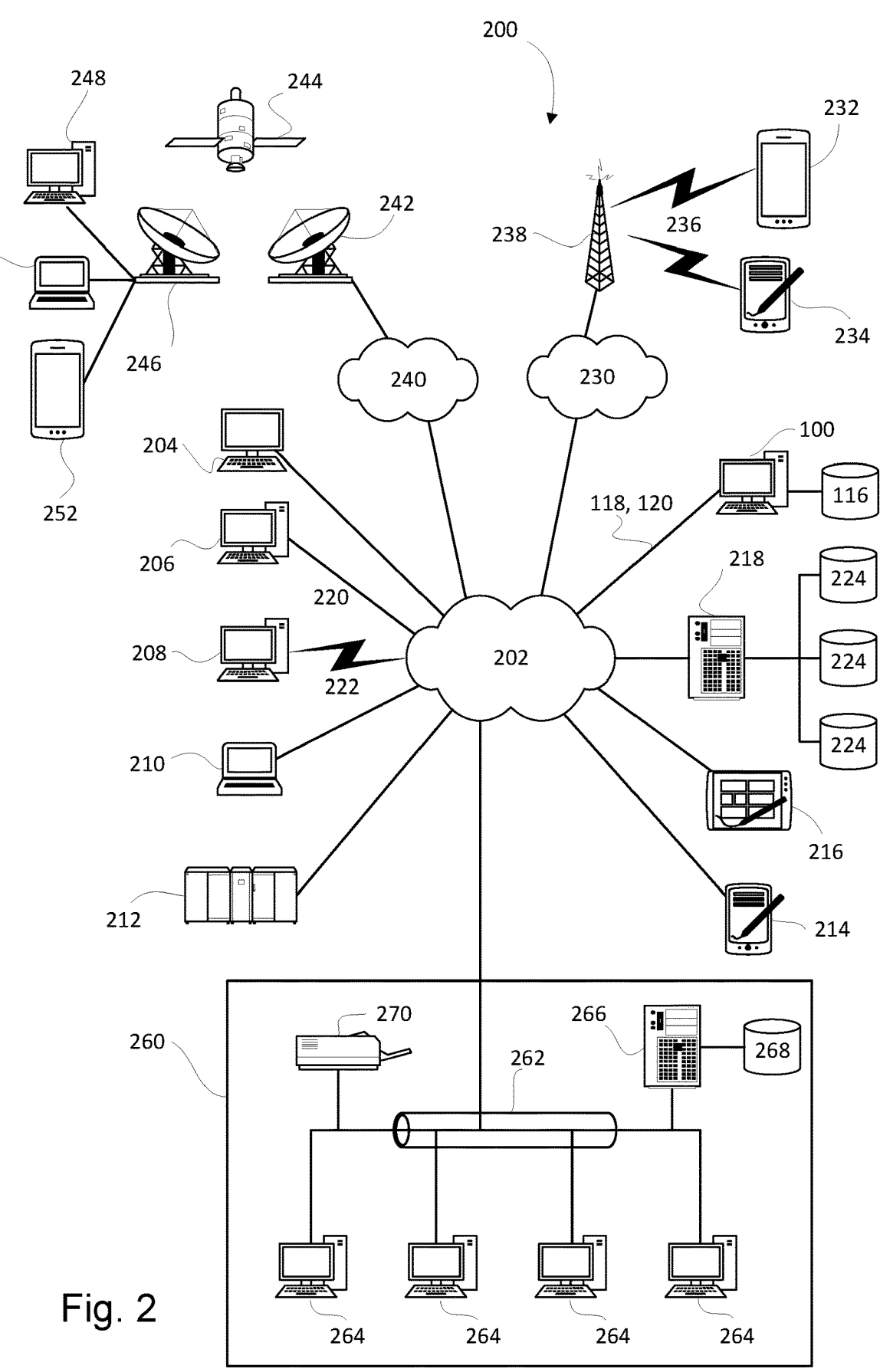
FIG. 2 illustrates an example network infrastructure that can be utilised to embody or give effect to a particular embodiment.

The processing system 100 may be a part of a networked communications system 200, as shown in FIG. 2. Processing system 100 could connect to network 202, for example the Internet or a WAN. Input data 118 and output data 120 could be communicated to other devices via network 202. Other terminals, for example, thin client 204, further processing systems 206 and 208, notebook computer 210, mainframe computer 212, PDA 214, pen-based computer or tablet 216, server 218, etc., can be connected to network 202. A large variety of other types of terminals or configurations could be utilised. The transfer of information and/or data over network 202 can be achieved using wired communications means 220 or wireless communications means 222. Server 218 can facilitate the transfer of data between network 202 and one or more databases 224. Server 218 and one or more databases 224 provide an example of an information source.

Other networks may communicate with network 202. For example, telecommunications network 230 could facilitate the transfer of data between network 202 and mobile, cellular telephone or smartphone 232 or a PDA-type device 234, by utilising wireless communication means 236 and receiving/transmitting station 238. Satellite communications network 240 could communicate with satellite signal receiver 242 which receives data signals from satellite 244 which in turn is in remote communication with satellite signal transmitter 246. Terminals, for example further processing system 248, notebook computer 250 or satellite telephone 252, can thereby communicate with network 202. A local network 260, which for example may be a private network, LAN, etc., may also be connected to network 202. For example, network 202 could be connected with ethernet 262 which connects terminals 264, server 266 which controls the transfer of data to and/or from database 268, and printer 270. Various other types of networks could be utilised.

The processing system 100 is adapted to communicate with other terminals, for example further processing systems 206, 208, by sending and receiving data, 118, 120, to and from the network 202, thereby facilitating possible communication with other components of the networked communications system 200.

Thus, for example, the networks 202, 230, 240 may form part of, or be connected to, the Internet, in which case, the terminals 206, 212, 218, for example, may be web servers, Internet terminals or the like. The networks 202, 230, 240, 260 may be or form part of other communication networks, such as LAN, WAN, ethernet, token ring, FDDI ring, star, etc., networks, or mobile telephone networks, such as GSM, CDMA, 4G, 5G etc., networks, and may be wholly or partially wired, including for example optical fibre, or wireless networks, depending on a particular implementation.

Figure 3:
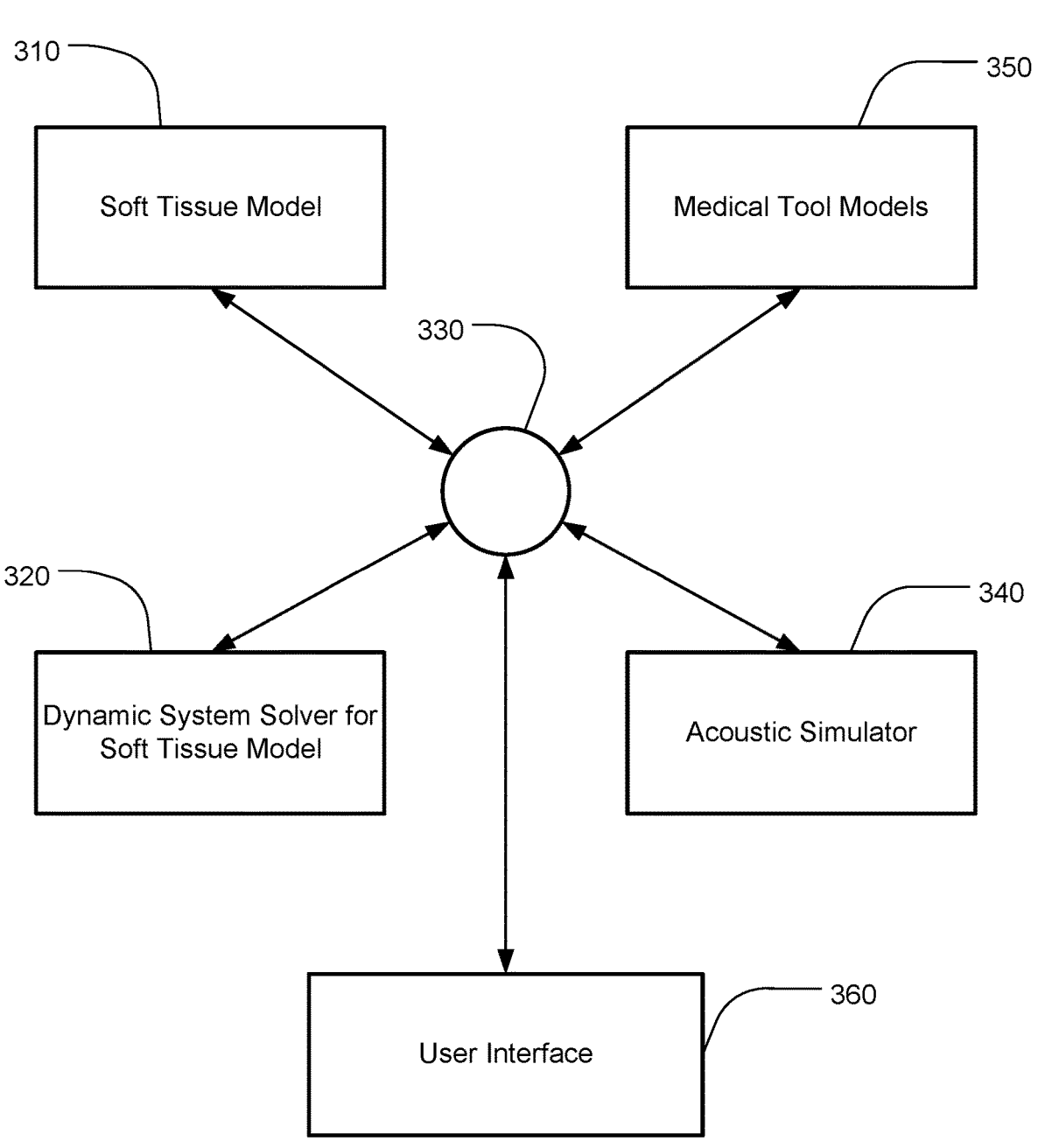
FIG. 3 illustrates a dynamic virtual ultrasound in accordance with one embodiment of the invention.

FIG. 3 shows modules that may form part of a dynamic virtual ultrasound 300. The modules of the dynamic virtual ultrasound 300 may be executed on a computer such as the processing system 100 communicating over the network 202. Alternatively, the dynamic virtual ultrasound 300 may be implemented on a dedicated hardware system customised for operation as a dynamic virtual ultrasound.

A first module of the dynamic virtual ultrasound 300 is a soft tissue model 310 where the tissue of a patient is modelled. The dynamic virtual ultrasound provides a soft tissue model of a patient, or a specific anatomical region of the patient, with which a user of the dynamic virtual ultrasound may interact using medical tools. The soft tissue model may be a volumetric model and in some instances may be a regular 3D voxel model. One advantage of using a volumetric model is that the model aligns with common data formats produced by a CT (Computerized Tomography) scanner or a MRI (Magnetic Resonance Imaging) scanner which may use DICOM (Digital Imaging and Communications in Medicine). The use of a common data format may allow data produced by CT and MRI scanners to form a basis for a soft tissue model with minimal pre-processing, allowing patient-specific data to be used.

The soft tissue model may be built upon a lattice or mesh such as a hexahedral or tetrahedral mesh. The mesh may be used to control deformation of the soft tissue model. The mesh is formed from cells, for example, each hexahedron or tetrahedron, with vertices of the mesh being a location of a particle. When using a position based dynamics solver, such as XPBD, soft bodies may be represented as particles located at vertices of the mesh of the soft tissue model, with the particles connected, or linked, together by constraints such as a contact constraint, distance constraint, volume constraint, position constraint, or other types of constraints. An example of such an arrangement may be seen in FIGS. 6A, 6B and 6C where tissue particles, such as the tissue particle 610, are connected together by constraints such as constraint 615. The soft tissue model may be built as follows.

First, a soft tissue model resolution is determined. The soft tissue model and the voxel model may have the same or different resolutions. For example, the voxel model may have voxels that are 0.5 mm in size, but a soft tissue model may have resolution of 2 mm as the spacing between particles.

In a second step, compressible parts of the soft tissue model, e.g., blood vessels, are connected with distance constraints to adjacent particles to form cells.

In a third step, incompressible parts of the model, e.g. soft tissue, organs, or bone, are connected with volume constraints to form cells. The use of volume constraints allow for conservation of volume for the incompressible parts of the soft tissue model.

In a fourth step, particles located in free space regions, e.g. air, of the soft tissue model are connected with very weak distance constraints so that the free space region has little influence on the soft tissue model. However, the presence of the free space regions of the soft tissue model allows the soft tissue model to be restored reliably after being compressed.

For the compressible and incompressible parts of the soft tissue model, a type and stiffness of material inside each of the cells of the mesh may be used, where stiffness refers to a tensile stiffness mechanical property of a material, which is quantified by Young's Modulus. The material stiffness values are used to constrain the solution from the position based dynamics solver. The type and material properties for a cell of the soft tissue model may be determined using a voxel model. That is, the voxels model is used to derive continuously varying material properties for the soft tissue model. The material property of the cell of the soft tissue model is found from the voxel model. For example, a density of the soft tissue model at a particular point in space can be determined by mapping coordinates in the soft tissue model to coordinates in the voxel model. The density of the soft tissue model can then be found using the density from the voxel model.

Material properties at a given voxel of the voxel model are defined by a transfer function:

$$M_{ijk} = F(i, j, k) \qquad (1)$$

Where: (i, j, k) identifies a voxel location in the voxel model and $M_{ijk}$ is material properties at the voxel. The material properties may include, but is not limited to, stiffness, compressibility and density. A transfer function represents a continuously varying function over a region of space and may be used to provide material properties at specific locations in space for use in the soft tissue model.

Defining the transfer function may be done based on data from a CT or MRI scanner. Some examples of how to determine the transfer function include the following. Firstly, material properties at all locations are known a priori and supplied as a separate voxel dataset. The transfer function simply looks up the material properties in the supplied voxel dataset. One alternative is to manually build the transfer function, mapping values from a CT and/or MRI scan to known material properties. In this example, all regions of bone will have the same material properties that may be found using a look up table.

A third alternative may be used for data provided from a CT scan. CT scan data has a relationship between measured intensity and material stiffness. A transfer function may be determined using data points that are of a known substance, such as bone, fat, muscle, and skin, and assign the material stiffness to the substance based on the CT scan intensity. Using the intensity value allows a transfer function to be created from CT scan data and linear interpolation may be used to generate stiffness values located between the intensity values, thus generating approximate stiffness values for each voxel.

Different transfer functions may be used within a soft tissue model/voxel model through the use of segmentation masks. Segmented spatial regions may use different transfer functions. In one example, segmentation masks may be used for regions where CT and/or MRI scan data values overlap for segments with different material properties.

A dynamic solver 320 is implemented as part of the dynamic virtual ultrasound 300 and makes modifications to the soft tissue model 310 based on interactions between the soft tissue model 310 and medical tools such as the ultrasound probe. The dynamic solver 320 uses a position based dynamic solver such as an extended position based dynamics (XPBD) or a variant, such as the Small Steps approach, to modify the soft tissue model 310. A position based dynamics solver may be fast to compute while being reasonably stable. Object positions are updated directly and the dynamic position based dynamics solver 320 calculates resulting velocities after constraining particles based on the distance or volume constraints. In some versions of the dynamic virtual ultrasound the dynamic position based dynamics solver 320 may also calculate acceleration and forces.

The modules of the dynamic virtual ultrasound 300 may communicate using a communications hub 330. The communications hub 330 is connected to each of the modules and may receive and transmit data to each of the modules. Data received by the communications hub 330 may be transmitted to an individual module or broadcast to each of the modules, with the module filtering out unrequired data. In an alternative arrangement of the dynamic virtual ultrasound 300, each module may be directly connected to other modules where transmission of data is required.

An acoustic simulator 340 forms part of the dynamic virtual ultrasound and may be used to generate the ultrasound image that is displayed to a user of the system. The acoustic simulator 340 uses ray tracing techniques to simulate propagation of ultrasound waves in the soft tissue model from the ultrasound probe. When using an ultrasound machine on a patient, artefacts are produced in the resulting imagery due refraction, reflection and absorption of the acoustic energy as the ultrasound interacts with soft tissue. Such artefacts may enhance realism when incorporated into the output of the dynamic virtual ultrasound. The acoustic simulator 340 of the dynamic virtual ultrasound 300 uses ray tracing techniques and applies ray tracing to a soft tissue model to generate the output image.

Although ultrasound propagates in three dimensions, performing ray tracing in 3D may be computationally expensive. The dynamic virtual ultrasound 300 may use an alternative approach to 3D ray tracing to reduce computational requirements and help maintain real-time performance of the dynamic virtual ultrasound 300. Instead of performing 3D ray tracing, ray tracing may be performed only in a plane defined by a position and orientation of the ultrasound probe. Limiting the ray tracing calculation to a plane may greatly reduce computational requirements at the expense of not including out-of-plane artefacts. However, such artefacts may not be significant in practice.

The output image produced by the dynamic virtual ultrasound 300 and displayed to the user of the dynamic virtual ultrasound 300 may be obtained by determining the image from slicing the soft tissue model with the plane defined by the position and orientation of the ultrasound probe. Pixel values for the output image may be obtained by the transfer function described above in relation to equation 1 of the soft tissue model 310. Specifically, the acoustic simulator 340 uses acoustic impedance from the soft tissue model at all locations in the output image to calculate refraction. As relative acoustic impedance may be used to calculate refraction, the relative acoustic impedance may be substituted for a quantity proportional to acoustic impedance. Acoustic impedance is proportional to density, which is one of the material properties of the transfer function of equation 1. The density of soft tissue is also related to intensity in a CT image, which allows the use of a CT image as the source of suitable proxy for acoustic impedance.

Medical tools, as described below in relation to tool models 350, may also be simulated as part of the dynamic virtual ultrasound 300. When a medical tool, such as a hypodermic needle, intersects the plane defined by the position and orientation of the ultrasound probe, the tool may be incorporated into the soft tissue model on which ray tracing is performed to generate the output image.

The dynamic virtual ultrasound 300 also includes the tool models 350. When using the dynamic virtual ultrasound a user may interact with tissue with a number of medical tools. The medical tools are dynamic objects modelled using particles and constraints in the position based dynamics solver. The constraints may be used in two ways. First, a tool may have internal constraints to model the tool. Secondly, interactions between a tool and the soft tissue model may be modelled with additional constraints between a particle of the tool and a particle of the soft tissue model.

Medical tools are dynamic objects that take part in the physics simulation of the dynamic virtual ultrasound. As a result, complex physical interactions between a tool and the tissue may be modelled. An example of a complex physical interaction is the way that a physician may retract and reposition a needle during a regional block procedure; the needle may not be moved arbitrarily as the needle position is constrained by the soft tissue.

Position constraints between a medical tool and soft tissue are handled using the position based dynamics solver in the dynamic virtual ultrasound 300. With suitable constraints created between particles in the medical tool and the soft tissue model, a tool may be positioned based on user input before the position based dynamics solver re-positions the tool. For the example of a physician retracting and repositioning a needle during a regional block procedure, the physician may attempt to move a simulated needle, using a virtual reality controller, in a way that is physically impossible, resulting in the simulated needle being "pushed back" by the position based dynamics solver, according to the soft tissue model, to a realistic location.

Haptic feedback may be generated by the dynamic virtual ultrasound 300 to signal a difference between user movement of a medical tool and an allowed position of the medical tool calculated by the position based dynamics solver. The haptic feedback may be used to align the medical tool, as controlled by the user, with the allowed position of the medical tool. One alternative to using haptic feedback to achieve co-location of the user's hands and the medical tools is to allow divergence between the location of the hands and the medical tool, but connect the two locations with virtual springs. In one example the virtual springs are modelled by distance constraints to pull the medical tool model in the direction of the hand's location. The result, once applied by the position based dynamics solver, is a force on the medical tool model in the direction of the hand's location.

Interaction between a medical tool and the soft tissue model may vary depending on a medical tool type. Examples of medical tool types include an ultrasound probe, a hypodermic needle, a cannula, a scalpel, sutures, dressing, and forceps.

An ultrasound probe may be represented in the soft tissue model as a rigid body with embedded particles that control a position of the ultrasound probe. Moving the ultrasound probe causes collisions between particles of the ultrasound probe and particles of the soft tissue model, although collisions with air particles cells may be ignored. The collisions result in the addition of contact constraints between the colliding particles of the soft tissue model and the particles of the ultrasound probe. The contact constraints allow the user to depress the soft tissue of the soft tissue model by pushing the probe. The depression simulates flattening of the skin of a patient under the probe to allow transducers of the ultrasound probe to make contact with the skin of the patient for effective operation of the ultrasound probe.

A user of the dynamic virtual ultrasound may also apply pressure, by pressing down on the ultrasound probe, to aid blood vessel identification. Under pressure from the probe, a vein will compress while an artery will not. The different behaviour between veins and arteries may be seen on an ultrasound display and is an important technique used in many ultrasound guided procedures. The use of volume constraints for incompressible tissue and distance constraints for compressible parts of the soft tissue model allows pressure applied at the skin to transfer to blood vessels and the blood vessels are able to collapse due to the blood vessels material properties. For a soft tissue model with suitable material properties of the different sections, a vein will collapse with less pressure applied than required to compress an artery.

Hypodermic needles and cannulas may be operated by a user of the dynamic virtual ultrasound. The simulation of needles and cannulas allows for regional block procedures to be simulated. As a needle is advanced through soft tissue, the needle drags the soft tissue due to friction between the needle shaft and the soft tissue. The friction between a needle, or cannula, and soft tissue is modelled by the position based dynamics solver and the soft tissue model.

A needle shaft may be represented in the soft tissue model as a rigid body with particles evenly spaced along the length of the shaft. As the needle advances through the soft tissue, distance constraints are added between particles on the needle shaft and adjacent particles of the soft tissue model. The distance constraints have a rest length equal to a distance between the particles at the beginning of a simulation time step. The needle is inserted further by the user, increasing the distance between constrained particles of the needle and soft tissue model. Next, the position based dynamics solver moves particles in the soft tissue model in order to satisfy the distance constraints. As described below, the constraints are discarded at the end of a simulation time step and new constraints are generated during a subsequent simulation time step. This approach allows needle retraction to be handled in the same manner as needle insertion as needle retraction is symmetrical to needle insertion. As a result, no special handling of needle retraction is necessary.

The position based dynamics solver takes into account the volume and distance constraints on the soft tissue model as well as the distance constraints between particles on the needle and the soft tissue model. Linking the needle particles and the soft tissue model particles allows for deformation of the soft tissue model by the needle while maintaining the physical properties encoded in the soft tissue model.

The use of distance constraints between the needle and soft tissue model particles provides a reasonable approximation of kinetic friction, which is a constant friction force when moving at a constant velocity. When a needle is moved at a constant velocity, in the dynamic virtual ultrasound, a constraint function of the distance constraints will return an approximately constant value because a difference between a constraint length before and after the needle is advanced will be approximately the same for all of the needle related constraints. A model of how kinetic friction between soft tissue and a needle shaft varies with velocity may be incorporated into the soft tissue model as all the relevant material properties are known. However, the dynamic virtual ultrasound may use a linear relationship between velocity and friction.

Figure 4:
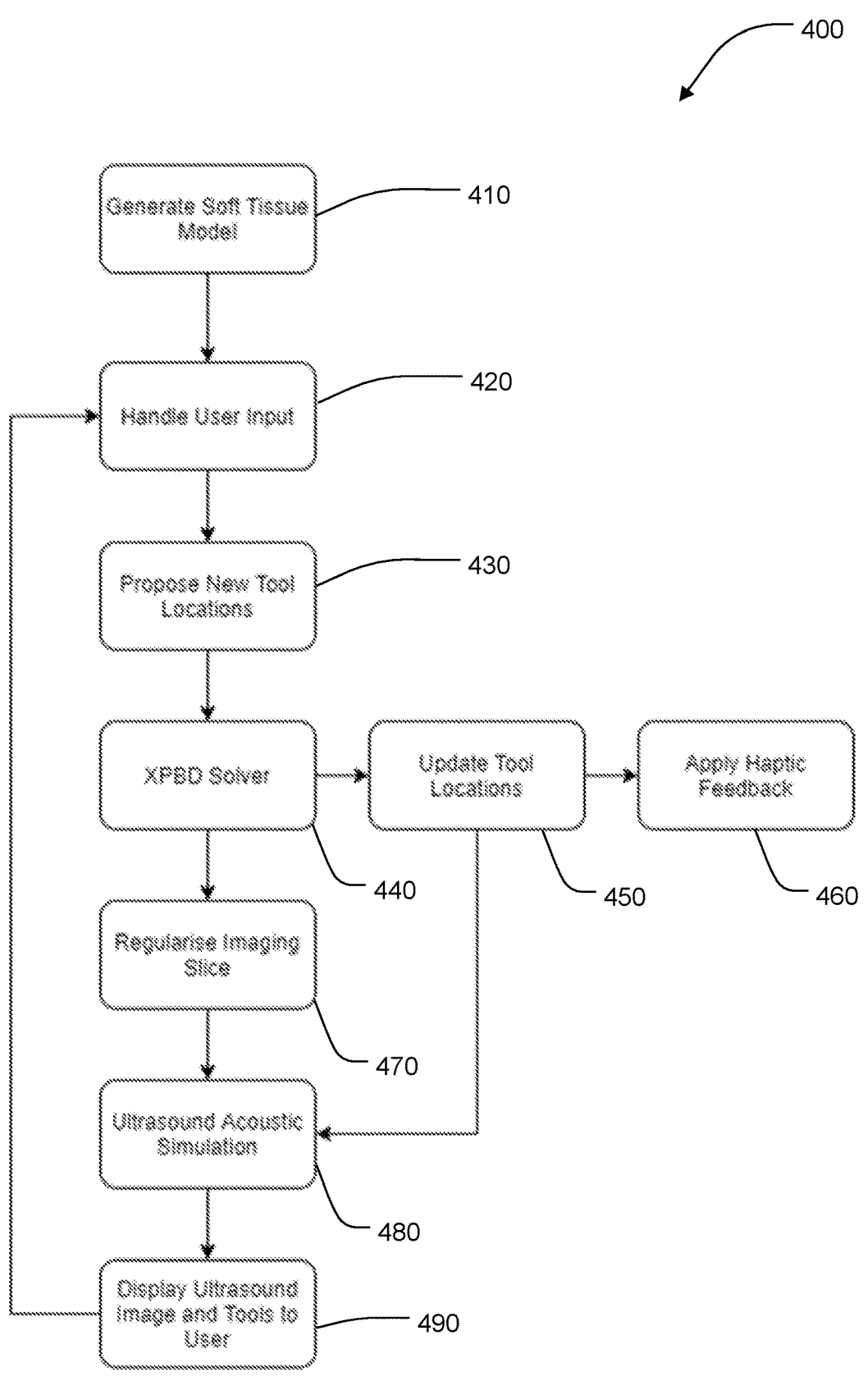
FIG. 4 illustrates a simulation workflow for operation of the dynamic virtual ultrasound of FIG. 3.
Figure 5A:
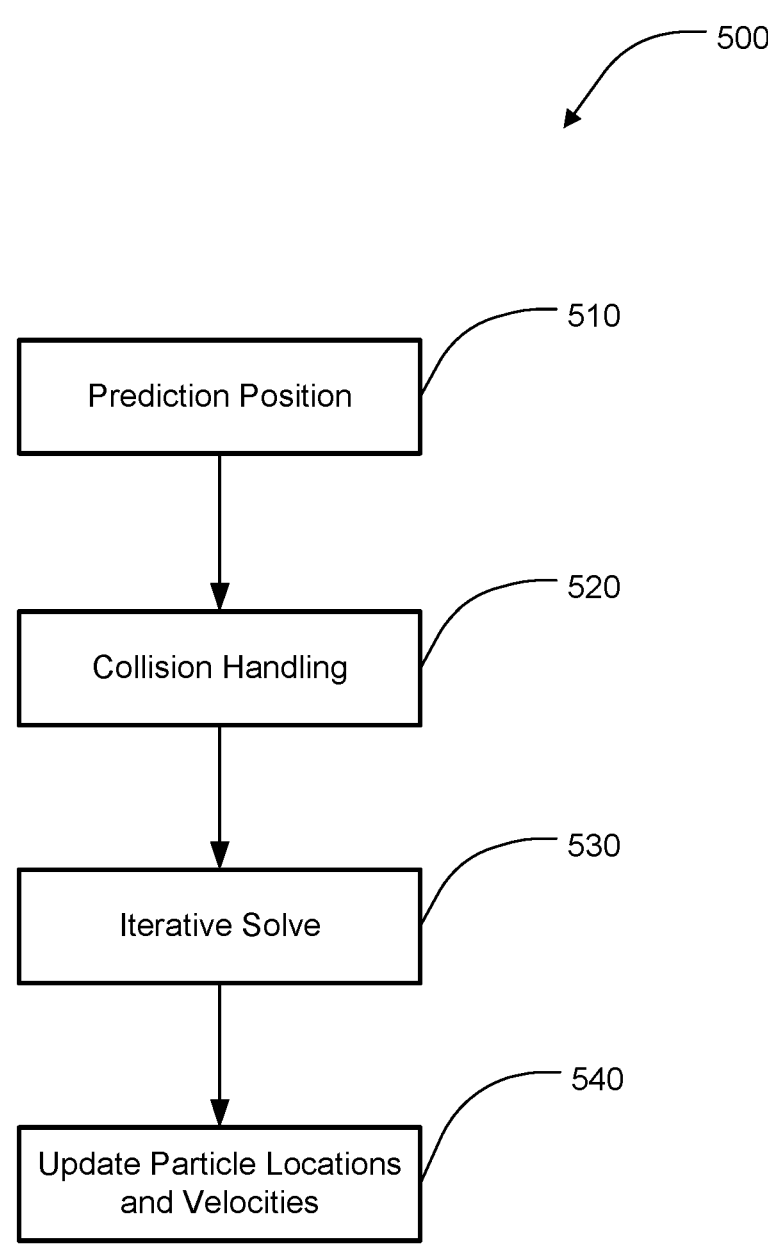
FIGS. 5A and B illustrate details of a position based dynamics solver of FIG. 4.
Figure 5B:
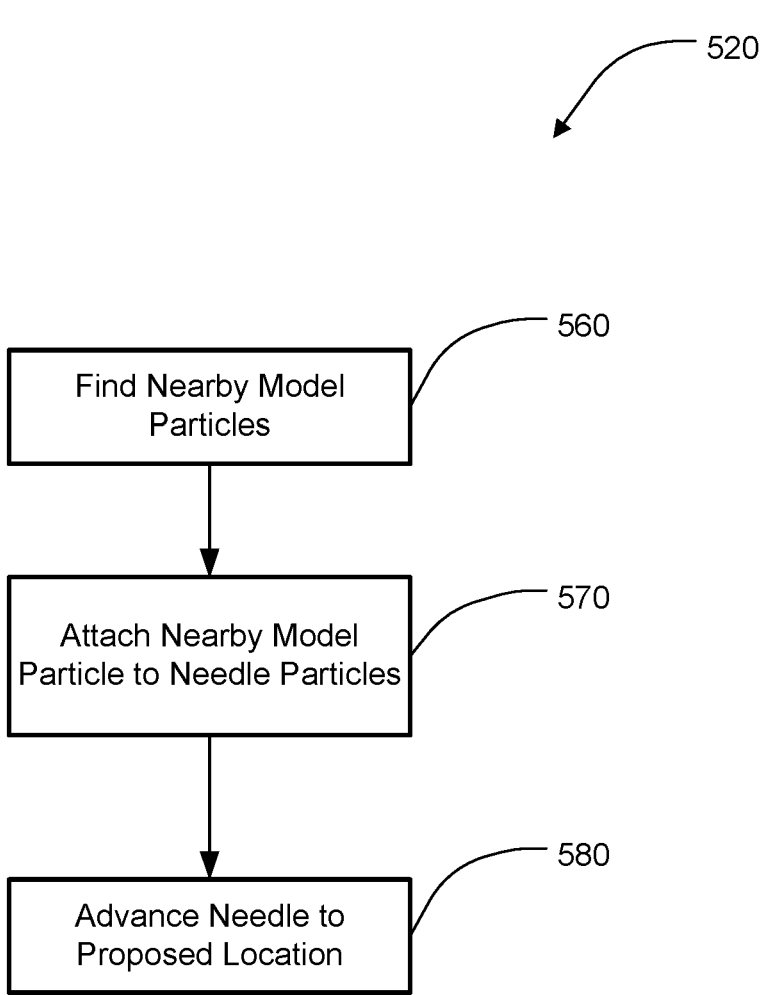

FIGS. 5A and 5B describe how needle interaction with a soft tissue model may be implemented within the simulation workflow 400 of FIG. 4. FIGS. 5A and 5B will be described below in more detail.

Any constraints added to handle the insertion of a needle or cannula may be discarded at the end of a simulation time step of the position based dynamics solver. As a result, the constraints are determined and added for any subsequent time step. As such, there is no need to remove, update or otherwise manage the lifetime of these constraints.

When needle velocity becomes zero, after deforming the soft tissue model, the soft tissue constraints will try to push the soft tissue back into an original undeformed state. The constraints between the needle and the nearby particles of the soft tissue model are still created for each time step, but the needle will not be advanced as the needle has zero velocity. However, the constraints between the needle and the soft tissue model will oppose the motion of the soft tissue, effectively applying friction to the movement of the soft tissue as the soft tissue returns to an undeformed state.

An example of needle insertion into a soft tissue model will now be described in relation to FIGS. 6A, 6B and 6C. The diagrams show a 2D deformation of a soft tissue model, although in practice the needle will be inserted into a 3D soft tissue model.

Figure 6A:
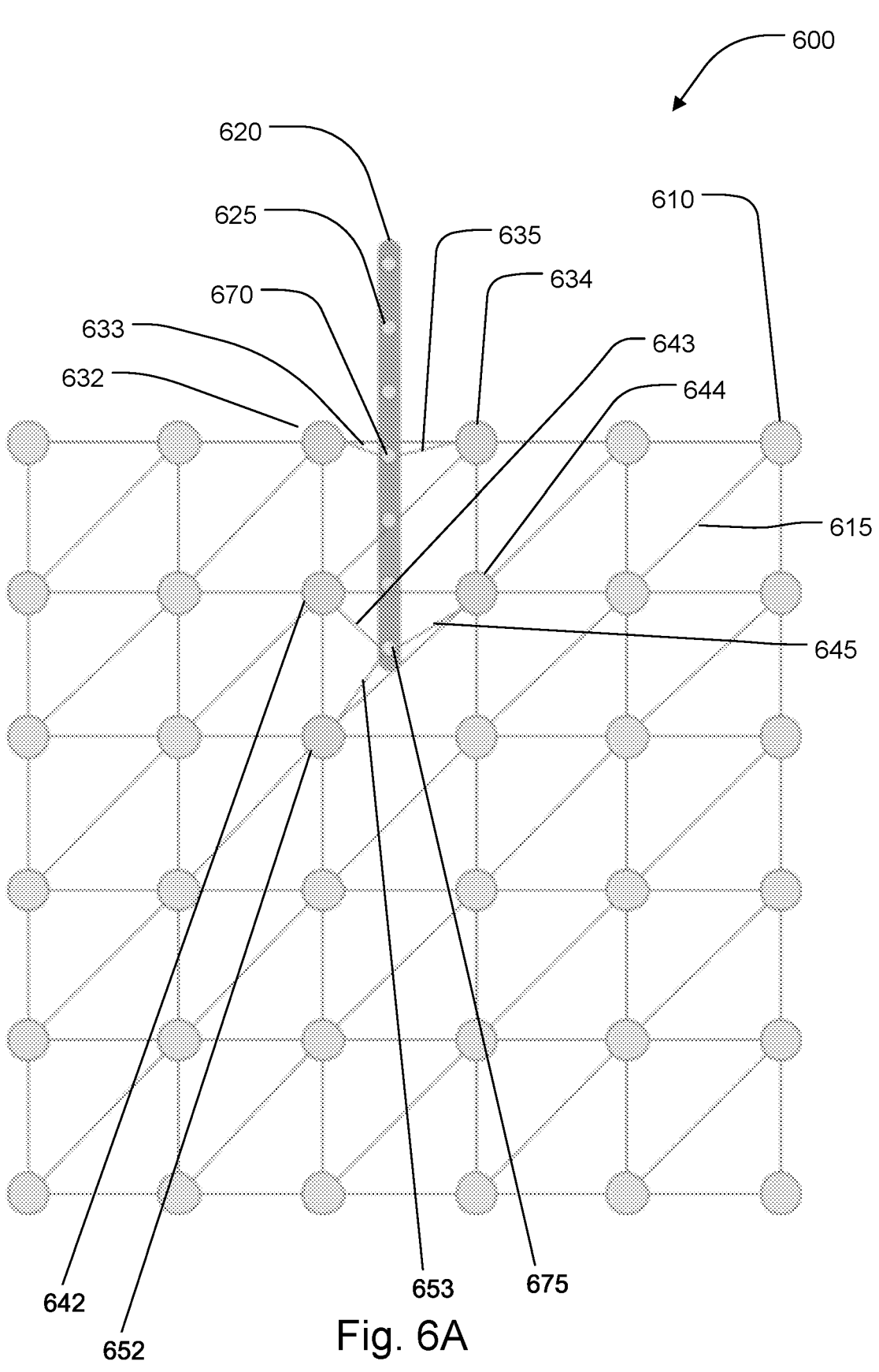
FIGS. 6A, B and C illustrate insertion of a needle into a soft tissue model according to the dynamic virtual ultrasound of FIG. 3.
Figure 6B:
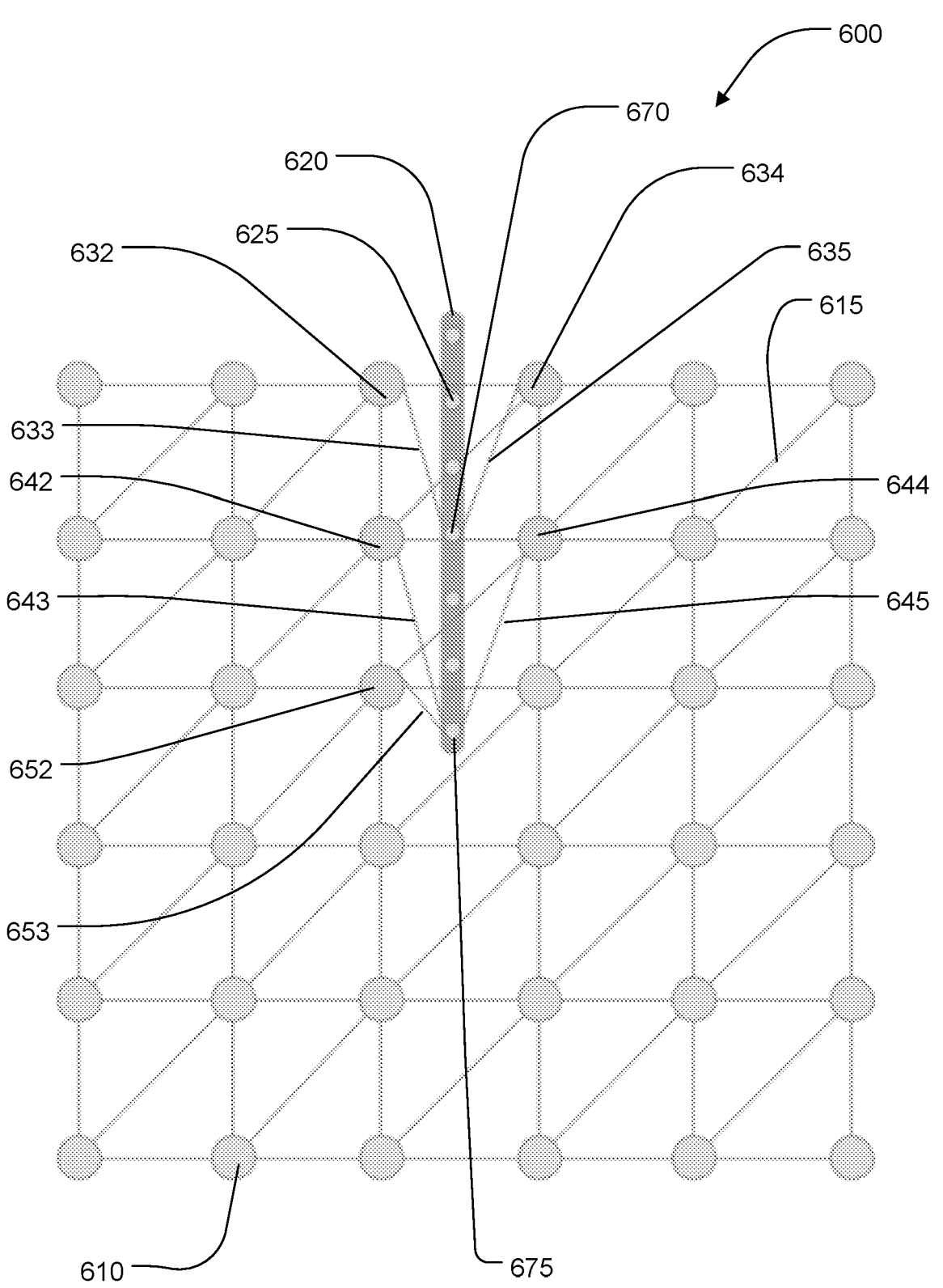
Figure 6C:
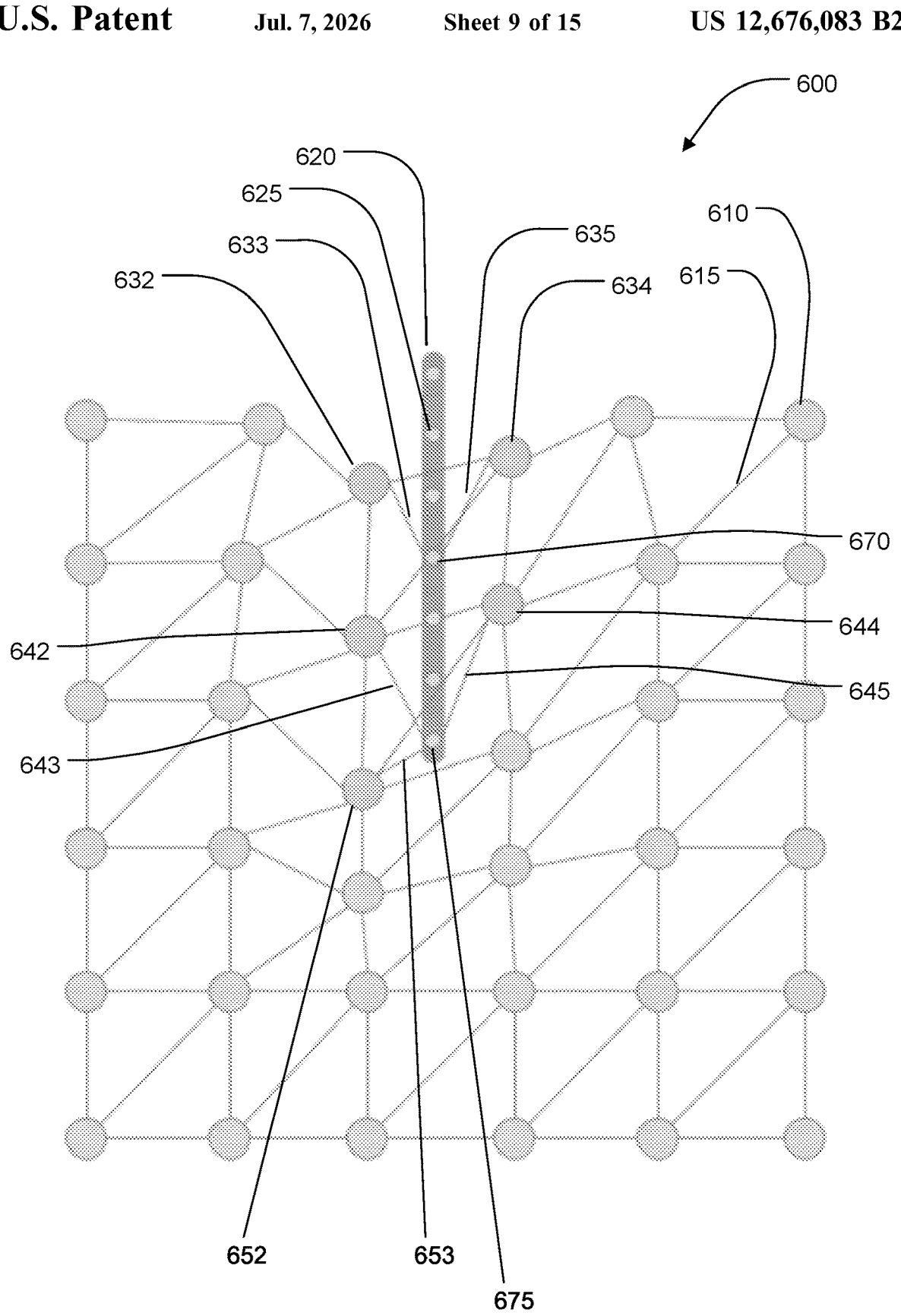

Although not shown in FIGS. 6A, 6B and 6C, the position based dynamics solver will not only move soft tissue particles, but will also move particles of the needle as the soft tissue will "push back" on the needle. That is, the soft tissue will apply a force to the needle particles through the constraints between the needle particles and the soft tissue model particles. When the needle is advanced, the force applied to the needle from the soft tissue is negligible. However, if the needle is moved laterally or pivoted (i.e. swung) by the user then there will be considerable push back from the soft tissue. The push back from the soft tissue model may result in a desired position of the needle, as set by the user, and an actual position of the simulated needle, determined by the position based dynamics solver, being different. As described above, the difference in position between the desired position and the actual position of the simulated needle may be communicated to the user using a feedback mechanism, such as haptic feedback.

Cutting of the soft tissue model by scalpels may be achieved by duplicating a particle that was shared between two cells so that each cell has an independent particle. This allows the two cells to separate where the particle was duplicated. If cutting is to be performed at locations between particles, then cells may be split to allow particles to be added at the appropriate locations. The use of a scalpel may also remove constraints between the duplicated or added particles where the scalpel has passed through the soft tissue model.

The dynamic virtual ultrasound 300 also has a user interface 360 for interactions with a user. The user interface 360 has an input and output aspect that may be implemented in different ways. A requirement for the user interface 360 is that the user is able to move medical tools, such as an ultrasound probe or a needle, in relation to the tissue and to see results of the ultrasound simulation. One way to implement the user interface 360 is to use a virtual reality interface where the user has a virtual reality view via goggles or a display screen. In a virtual reality system the user may provide input through the use of gloves, worn by the user, or handheld controllers, to provide position information for one or two hands of the user. An alternative approach is for the user to pick up an object of the tool, such as a proxy or dummy tool. A position and orientation of the object may be tracked by cameras that form part of the dynamic virtual ultrasound 300 and the position of the object incorporated into the virtual environment. An alternative to a virtual reality approach is to use augmented reality where virtual reality components may be added to a scene. In an augmented reality approach the patient, tools and scan output may be overlaid on a physical environment.

The user interface 360 may include physics-based interactions, where possible, to assist in providing a realistic simulation. Object positions, such as a medical tool position, may be updated directly and the position based dynamics solver calculates resulting velocities, and force or acceleration if required, after constraining object positions based on the model constraints.

A simulation workflow 400 for the dynamic virtual ultrasound will now be described in relation to FIG. 4. The simulation workflow 400 may be practiced on a computer such as the processing system 100. The simulation workflow 400 starts with receiving a soft tissue model step 410. As described above, CT or MRI scans may be used to generate the soft tissue model. Generation of the soft tissue model may be performed outside of the dynamic virtual ultrasound or, in some implementations, the soft tissue model may be generated by the dynamic virtual ultrasound.

Next, at a receive user input step 420, the simulation workflow 400 may receive input from a user of the dynamic virtual ultrasound. The user input for the dynamic virtual ultrasound is described above in relation to the user interface 360 of the dynamic virtual ultrasound 300. A new position of an ultrasound probe, and/or other medical tools, is determined by the user interface 360 at a determine new tool location step 430. The new position is determined from an output of the receive user input step 420.

At an apply position based dynamics solver step 440 a position based dynamics solver, such as XPBD, may be applied to the soft tissue model, including the tool position information from the determine new tool location step 430. The apply position based dynamics solver step 440 may operate as described above in relation to the dynamic position based dynamics solver 320.

Execution of the simulation workflow 400 may be parallelised by using two or more threads when executing on the processing system 100. In one example, a first of the threads interacts with the user and proceeds to an update location step 450 where the location of the tool may be updated. As described above, the location of the tool may be updated after the position based dynamics solver determines a position for the tool. The determined position may be different to the position set by the user. One example in which this situation may occur is when the soft tissue model pushes back on a medical tool to reposition the tool. The medical tool position set by the user in the receive user input step 420 is different due to the soft tissue model pushing on the tool. The user interface of the simulation workflow 400 may indicate the updated position of the tool to the user, as described above in relation to the user interface 360. For example, the updated position of the medical tool may be signalled to the user of the dynamic virtual ultrasound using haptic feedback in an apply feedback step 460.

A second of the threads may execute a regularise image slice step 470 and may be executed by the processing system 100. At the regularise image slice step 470 a slice is sampled of the soft tissue model from the receive soft tissue model step 410 and the resulting sliced regularised. The regularise image slice step 470 is performed because ray-tracing a deformed soft tissue model may be computationally expensive compared to ray-tracing a regular soft tissue model. Image slicing is performed along a plane defined by the ultrasound probe on the deformed soft tissue model. The regularised slice is an image of a cross section of the soft tissue model. An image, i.e. a 2D image of pixels, of the slice is formed and material properties of the deformed soft tissue model at each pixel of the image is sampled. The result is a regular 2D image containing the material properties across the slice. The regularised slice is in a form that allows efficient ray tracing. A mechanism for sampling the soft tissue model at a given pixel location, which corresponds to a point in the 3D model space, uses baricentric coordinates of a sample point in a deformed cell of the soft tissue model containing the sample point. The sample point is mapped back to the undeformed soft tissue model. Once mapped to the undeformed soft tissue model the sample point can be mapped to the (i, j, k) space of the input data where the transfer function of equation 1 may be used to evaluate the material properties for the sample location.

A number of acoustic anomalies may occur during ultrasound scanning when a medical tool is inserted into a patient. Such acoustic anomalies may include acoustic shadowing, specular reflections, beam width and side lobe artefacts, needle bevel reflection, and reverberations that include comet tails. An example of an acoustic anomaly created by a medical tool are reverberations created by needles and guidewires. Specular reflections off needles and guidewires when they are near another strong reflector, such as the boundary of a blood vessel, can cause reverberations because acoustic energy reflects back and forth between the tool and the strong reflector before being transmitted back to the ultrasound probe. In the case of a large gauge needle, reverberation can happen within the hollow needle shaft, giving rise to comet-tail artefact that helps identify the needle in short-axis techniques and causes familiar reverberation stemming from the needle shaft in long-axis techniques. Examples of medical tools that are inserted into the soft tissue include hypodermic and echogenic needles, cannulas, guidewires and catheters.

Acoustic anomalies may be reproduced in the dynamic virtual ultrasound as part of the simulation workflow 400. Material properties of any medical tools intersecting the image slice may be incorporated into the 2D image formed in the regularise image slice step 470. As described above, the transfer function of equation 1 may be used to evaluate the material properties for the sample location for each pixel of the image. Incorporating medical tools is done by checking each pixel in the image to determine if a location of a current pixel is inside any part of a medical tool. If the current pixel is determined to be inside a medical tool, the material properties of the tool are used for the pixel, instead of the material properties of the soft tissue model. The material properties of the medical tool may be determined using a transfer function based on the tool, similar to the transfer function of equation 1. Such an approach results in the medical tools being incorporated into the acoustic simulation and produces the acoustic anomalies. The acoustic simulation does not need to treat medical tools explicitly. Because the material properties of the tools are captured in the 2D image that is ray traced, the medical tools, and any anomalies they create, are produced as part of the acoustic simulation.

At an ultrasound simulation step 480 the imaging slice from the regularise image slice step 470 and the updated tool locations from the update location step 450 are combined before the ultrasound simulation is performed. The updated location of the medical tool, or tools, from the update location step 450 is used as the tool location, instead of the proposed tool location from the determine new tool location step 430, as the updated location of the medical tool takes into account forces applied to the medical tool by the soft tissue model. The ultrasound simulation is performed as described above in relation to the acoustic simulator 340.

Once the ultrasound simulation step 480 has generated the ultrasound image, the image is displayed to the user of the dynamic virtual ultrasound at an output to user step 490. The ultrasound image, as well as information relating the positions of any medical tools, are displayed according to the selected user interface. As described above, in relation to the user interface 360, the ultrasound image and the medical tool information may be displayed using a virtual reality headset. Alternatively, the medical tool may be physical tool that has position information provided to a user using haptic feedback and the ultrasound image is displayed using a conventional monitor.

The simulation workflow 400 may return to the receive user input step 420 and loop to receive updated information from the medical tools, update the position based dynamics solver and display updated information to the user.

A position based dynamics solver 500, that may be used at the apply position based dynamics solver step 440 of the simulation workflow 400, will now be described in relation to FIG. 5A. The position based dynamics solver 500 is described for use with an ultrasound probe and a tool, such as a needle, and may be practiced on a computer such as the processing system 100 communicating over the network 202.

A first step of the position based dynamics solver 500 is a predict position step 510, where positions of particles are predicted based on velocities calculated from a previous simulation time step and external forces, such as gravity. At a collision handling step 520 additional constraints are added between particles of the tool and particles of the soft tissue model. The additional constraints are used to modify the soft tissue model based on movement of the particles of the tool as the tool interacts with the soft tissue. An example of additional constraints used with a needle and a soft tissue model will be described below in relation to FIGS. 6A, 6B and 6C.

Once collisions between the tool and the soft tissue model has been dealt with in the collision handling step 520, updates are made to the soft tissue model at an iterative solve step 530 where the position based dynamics solver processes the particles and constraints of the soft tissue model as well as the particles and constraints between the tool and the soft tissue model. Once the iterative solve step 530 has converged to a solution, the position of the particles in the soft tissue model and the tool are updated at an update step 540. Velocity may also be determined as displacement between the old and new positions of particles is determined with a known time period between the old and new positions.

Further details of the collision handling step 520 specific to needle interaction will now be described with reference to FIG. 5B. The collision handling step 520 may be practiced on a computer such as the processing system 100 communicating over the network 202 and be performed in three steps. A first step is a find nearby particles step 560 where particles near to the needle particles are located. The location of nearby particles may be based on locating a nearest particle in the soft tissue model. An alternative is to locate all particles of the soft tissue model located within a predetermined distance. In addition to distance, a direction of movement of the needle may also be taken into consideration for the selection of particles of the soft tissue model. In one example, particles of the soft tissue model close to the needle and in front of the needle particle, based on the direction of movement of the needle, may be selected. One way to select the particle is to form a plane through the needle particle, with the needle being a normal to the plane. The particles in the soft tissue model located on or behind the plane, based on the direction of movement of the needle, may be selected. The result is that a particle of the needle is attached to a particle of the soft tissue model that the needle particle has moved past. If there is no particle on the needle in a suitable location, then a particle of the soft tissue model may be connected to a particle located at a tip of the needle. Selecting a particle of the soft tissue model that the needle particle has passed and linking with constraints may effectively model friction forces between the needle and the soft tissue.

An attach particles step 570 may then be performed between a particle of the needle and the nearby particles selected in the find nearby particles step 560. The needle particles and the soft tissue model particle may be attached with distance constraints. Finally, at a move needle particles step 580, the needle is moved to a new location. As described above, the iterative solve step 530 will determine new locations for the soft tissue model particles as well as new locations for the needle particles based on the movement of the needle.

When the position based dynamics solver is a XPBD solver the addition of constraints may be performed during normal XPBD collision handling. The additional constraints are discarded at the end of each simulation. The additional constraints are required to be re-added for each simulation time step.

An example of a needle being inserted into a soft tissue model will now be described in relation to FIGS. 6A, 6B and 6C. The three figures show the progress of a simulated needle as the needle is inserted into a soft tissue model over a single simulation time step with FIG. 6A and FIG. 6B showing progress of the needle into the soft tissue model and FIG. 6C showing deformation of the soft tissue model caused by the needle. The deformation of the soft tissue model is determined at the end of the simulation time step. The deformation of the soft tissue model and the position of the needle may be shown on an output display to a user when an ultrasound scan of the soft tissue model and needle is generated.

A soft tissue model 600, as used in the dynamic virtual ultrasound, will now be described in relation to FIG. 6. The soft tissue model 600 has tissue particles, such as tissue particle 610, linked by one or more constraints such as constraint 615. While the soft tissue model 600 is shown as a two dimensional representation, for the sake of simplicity, the actual model used in the dynamic virtual ultrasound is three dimensional.

A simulated needle 620 is shown as being partially inserted into the soft tissue model 600. That is, the needle 620 has passed through the soft tissue particles and the constraints between the soft tissue particles. The needle 620 has needle particles 625, 670 and 675. The needle 620 is at rest and the soft tissue model 600 is in an undeformed state. A user of the dynamic virtual ultrasound has advanced the needle 620 and the movement will be reflected in deformation of the soft tissue model 600 and the simulated needle 620 position.

As part of the position based dynamics solver collision handling, nearby particles of the soft tissue model 600, such as tissue particles 632, 634, 642, 644 and 652, are determined. The nearby particles are located either adjacent to, or within a predetermined distance of, the needle 620. For each of the nearby particles, a distance constraint such as tissue needle distance constraints 633, 635, 643, 645 and 653 are formed between the nearby particles and a nearest particle on the needle 620. The constraints are attached between a soft tissue model particle and a needle particle located ahead, with respect to a direction of movement of the needle 620, of the soft tissue particle. If there are no particles on the needle 620 positioned ahead of the soft tissue particle then the soft tissue particle may be attached to a tip of the needle 620.

FIG. 6B shows an update to the soft tissue model 600 used in the dynamic virtual ultrasound where the needle 620 has been pushed further into the soft tissue model 600 to a proposed needle location. That is, the needle 620 has advanced further into the soft tissue model 600 when compared to the needle 620 of FIG. 6A. The movement of the needle 620 between FIGS. 6A and 6B increases a length of the tissue needle distance constraints 633, 635, 643, 645 and 653 added in FIG. 6A. During a next iteration of the position based dynamics solver the tissue needle constraints 633, 635, 643, 645 and 653 will pull on the tissue particles 632, 634, 642, 644 and 652 to further deform the soft tissue model 600.

FIG. 6C shows a further update to the soft tissue model 600 used in the dynamic virtual ultrasound where the effect of executing the position based dynamics solver is shown. The position based dynamics solver converges on a solution that best satisfies both the constraints in the soft tissue model 600, such as the constraint 615, and the tissue needle constraints 633, 635, 643, 645 and 653. The result is that the soft tissue of the soft tissue model 600 has been deformed, when compared to FIG. 6B, as the particles of the soft tissue model 600 are moved by constraints with the needle 620.

Figure 7A:
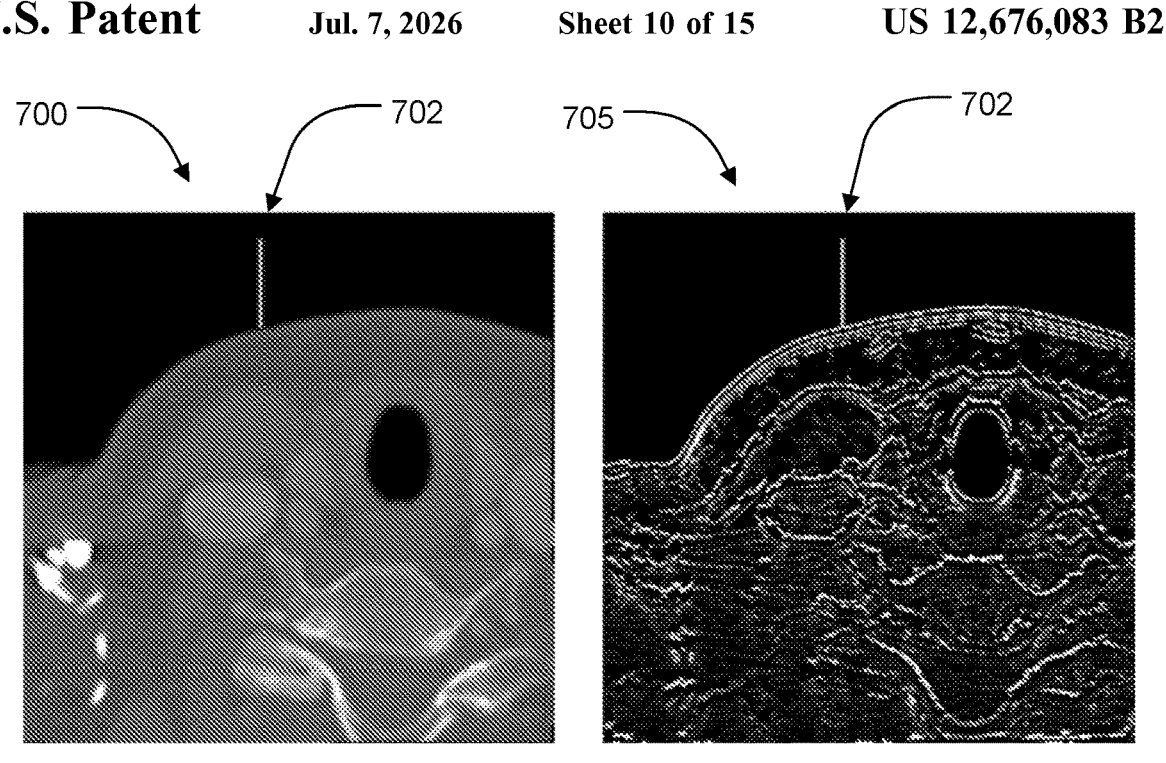
FIGS. 7A, 7B, 7C, 7D, 7E and 7F illustrate output images from the dynamic virtual ultrasound of FIG. 3.

Examples of a dynamic virtual ultrasound output with a needle will now be described in relation to FIGS. 7A, 7B, 7C, 7D, 7E and 7F. Each of the figures has a simulated CT scan image shown on the left and a simulated ultrasound image shown on the right. FIG. 7A shows a needle 702 touching the skin, as seen in simulated CT image 700 and simulated ultrasound image 705. The soft tissue model is generated using a CT scan of the neck of a patient with the simulated CT image 700 being a reconstructed slice through the CT data, taking into account any deformations made to the model. The simulated ultrasound image 705 is a simulated ultrasound image produced from the simulated CT image 700, with edges enhanced and noise reduced to allow anatomical features to be easily identified.

Figure 7B:
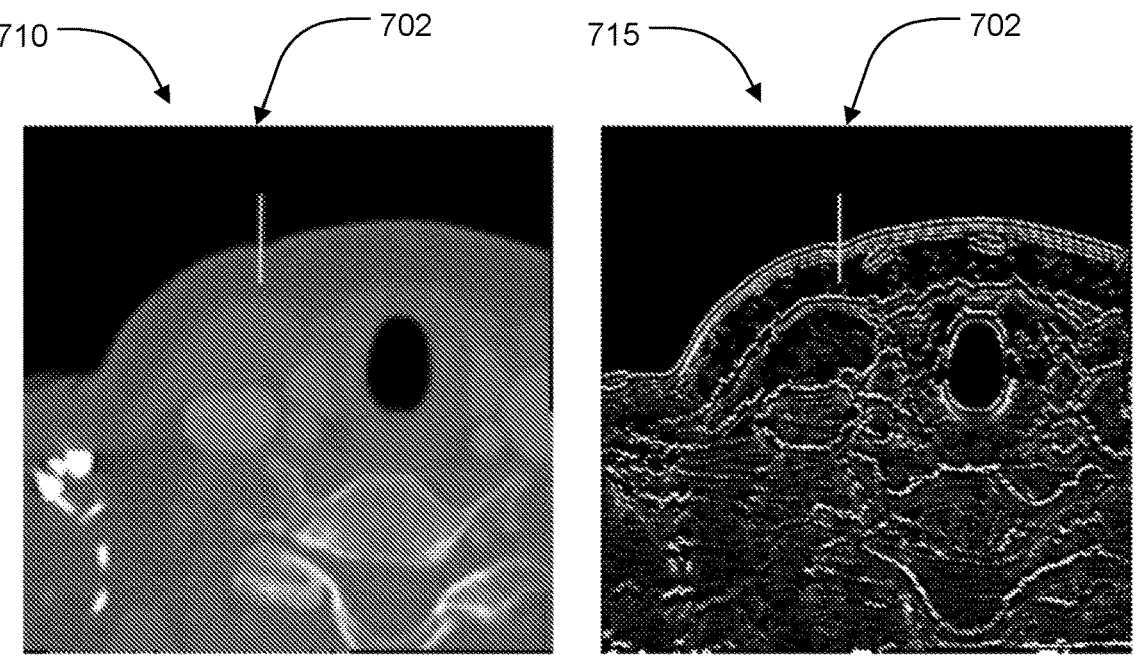

A simulated CT image 710 and simulated ultrasound image 715 of FIG. 7B show the needle 702 has advanced when compared to FIG. 7A. As the needle moves, friction between the soft tissue and the needle 702 drags the soft tissue. The deformation is most evident at the skin where an indentation has been made. The deformation is caused by constraints between the needle particles and the soft tissue model particles.

Figure 7C:
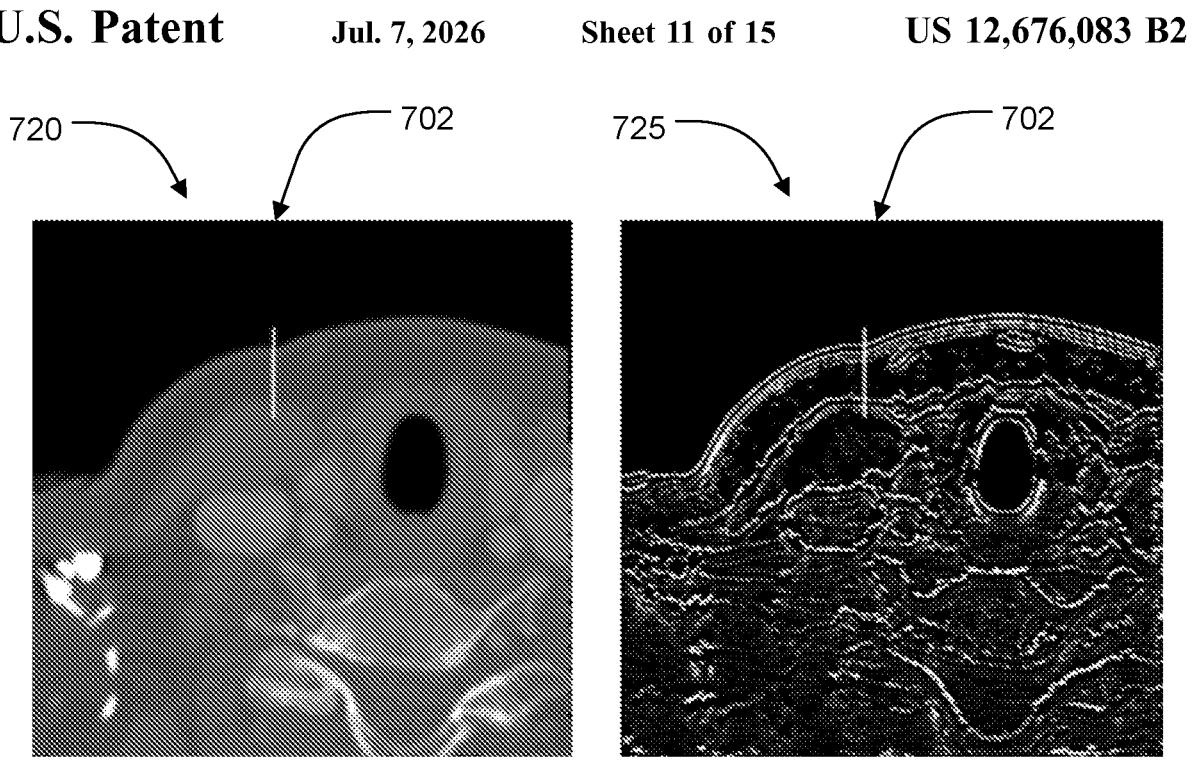

A simulated CT image 720 and a simulated ultrasound image 725 are shown in FIG. 7C where the needle 702 has advanced further. The needle 702 has entered the Stemocleidomastoid muscle and deformation at the stemocleidomastoid surface is apparent.

Figure 7D:
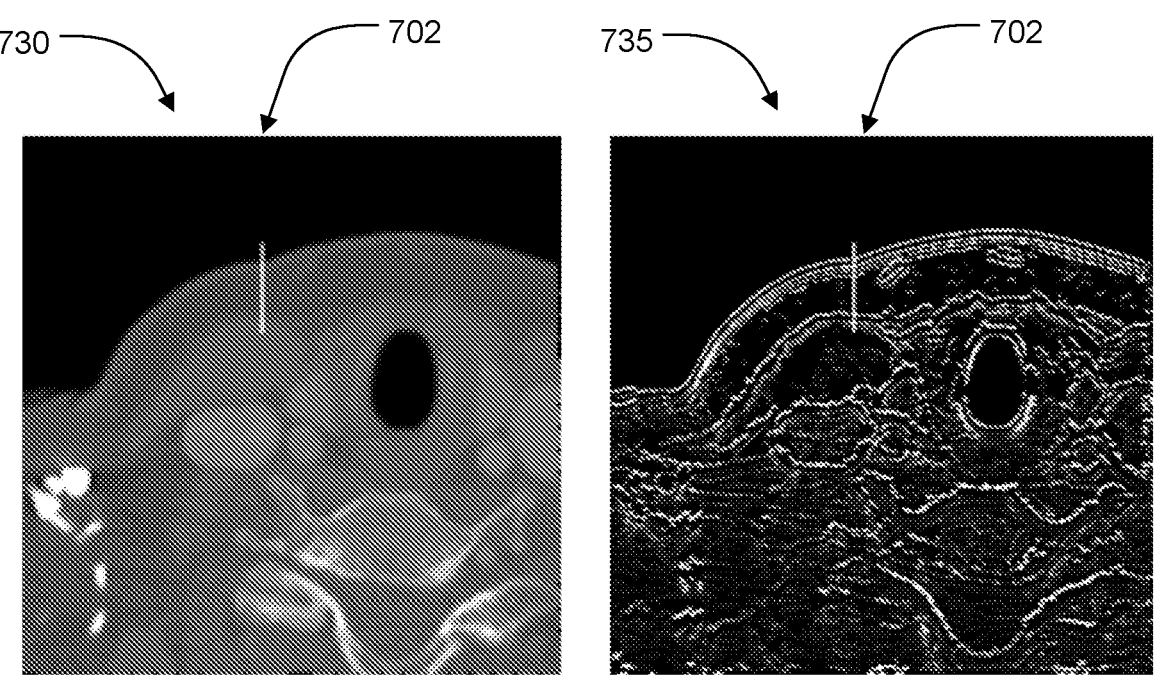
Figure 7E:
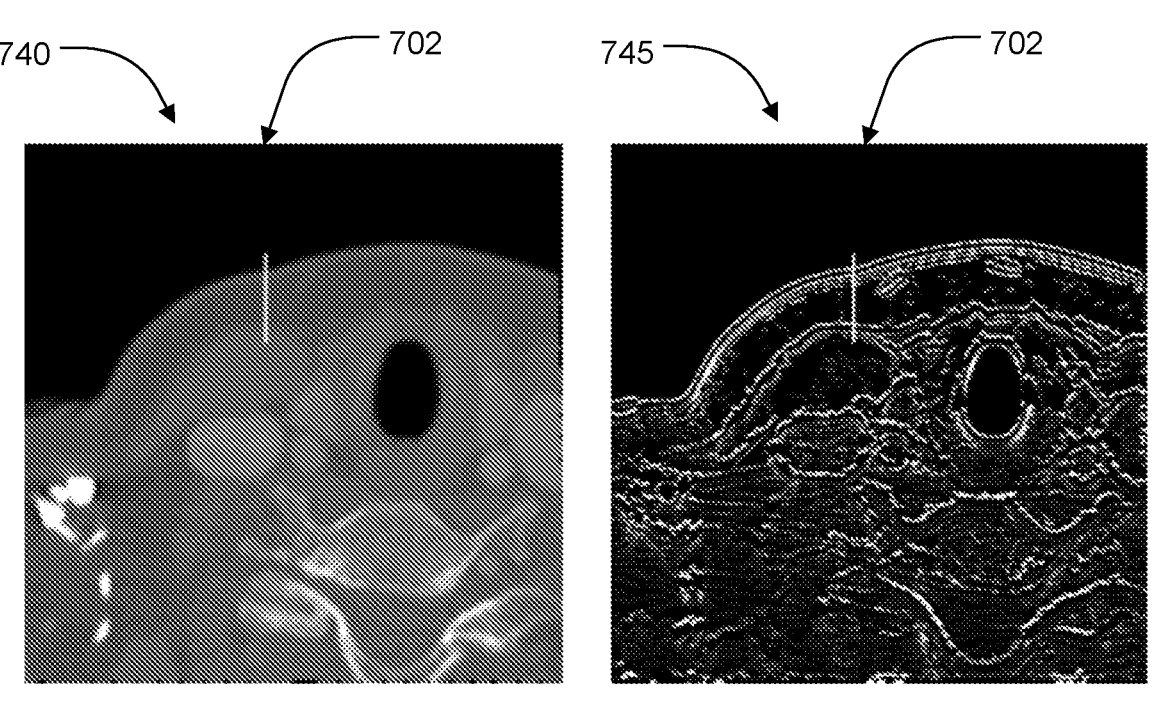
Figure 7F:
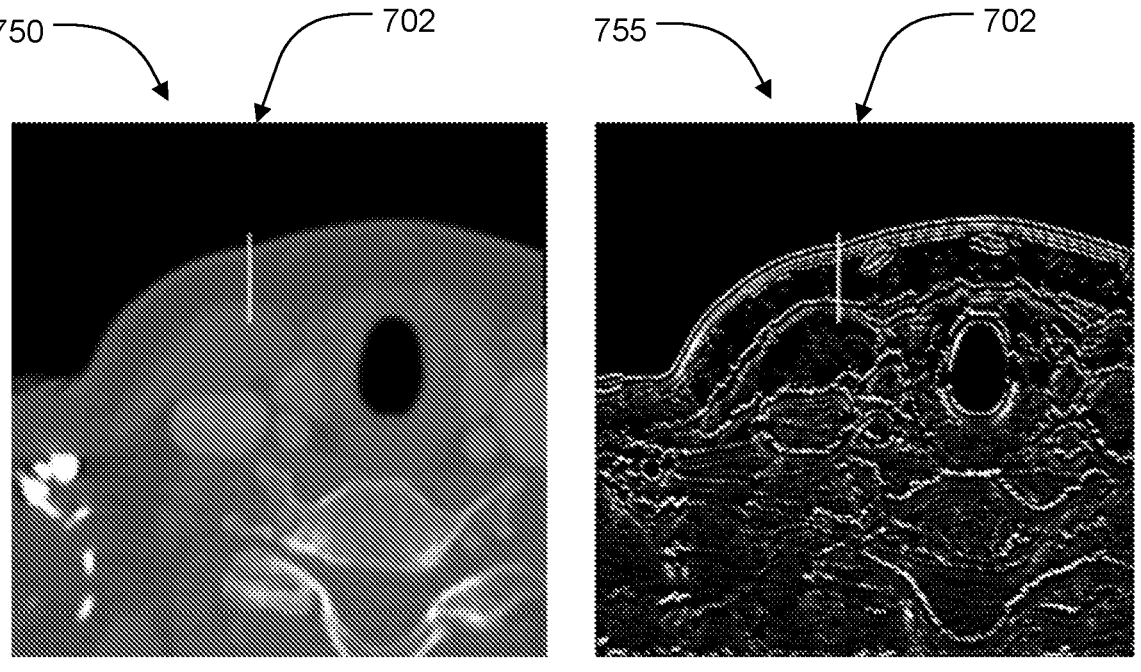

A sequence of simulated CT images 730, 740 and 750 as well as a simulated sequence of ultrasound images 735, 745 and 755 are shown in FIGS. 7D, E and F where the needle 702 advancement is stopped and the deformed soft tissue returns approximately to an undeformed state. This may be seen at the skin where the indentation is reversed in FIG. 7F.

Examples of a dynamic virtual ultrasound output with an ultrasound probe 802, represented by a horizontal line showing a leading edge of the ultrasound probe 802, will now be described in relation to FIGS. 8A, 8B, 8C and 8D. Each of the figures has a simulated CT scan image shown on the left and a simulated ultrasound image shown on the right.

Figures 8A, 8B:
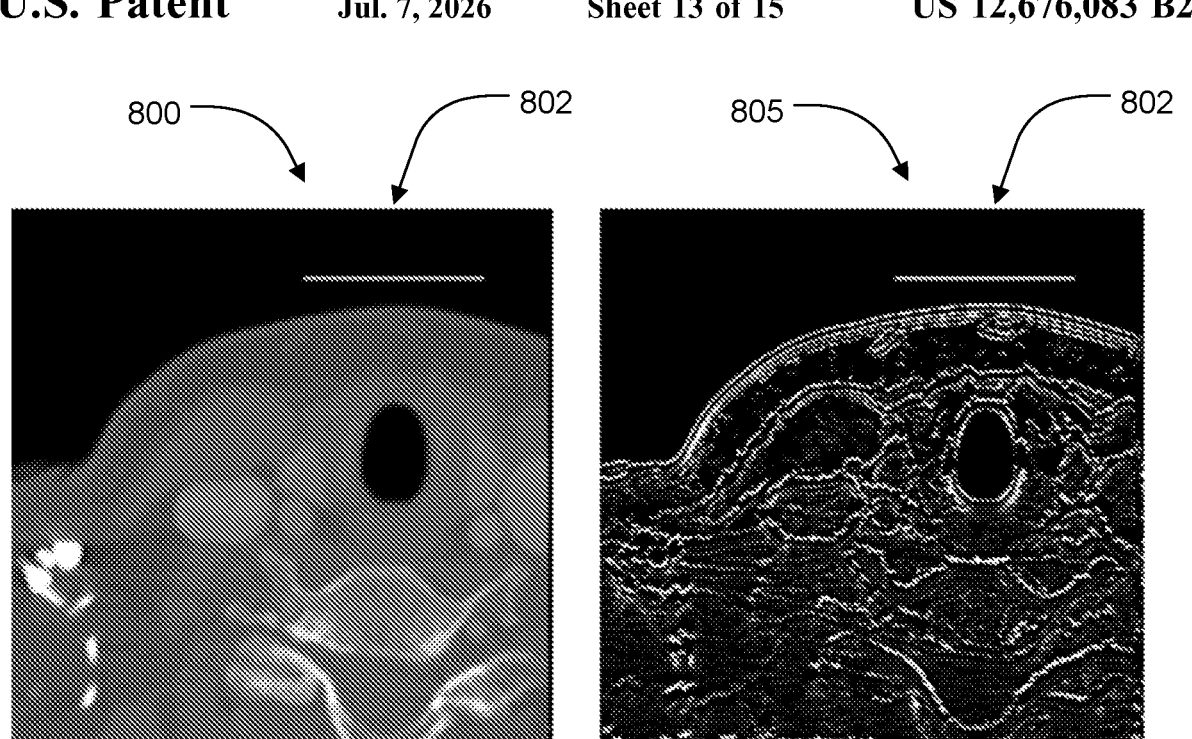
FIGS. 8A, 8B, 8C and 8D illustrate output images from the dynamic virtual ultrasound of FIG. 3.

FIG. 8A shows a simulated CT image 800 and a simulated ultrasound image 805. The source of the soft tissue model is a CT of the neck of a patient. A soft tissue model is constructed using mechanical properties derived from the CT scan data. In the soft tissue model used to generate the images of FIGS. 8A, 8B, 8C and 8D the soft tissue is non-compressible and volume preserving, while regions of air are compressible. The simulated CT image 800 is a reconstructed slice through the soft tissue model, taking into account the deformations made to the model by the ultrasound probe 802. The simulated ultrasound image 805 is a simulated ultrasound image produced from the simulated CT image 800, with edges enhanced and noise reduced to allow anatomical features to be easily identified. Note that normally only an area directly under a transducer of the ultrasound probe 802 would be displayed as output of the dynamic virtual ultrasound.

FIG. 8B shows the ultrasound probe 802 placed against the skin with light pressure in a simulated CT image 810 and a simulated ultrasound image 815. The ultrasound probe 802 flattens the skin and makes good contact between the ultrasound probe 802 and the skin. Soft tissue layers between the ultrasound probe 802 and the trachea, the black oval below the ultrasound probe 802, have not compressed, whereas the trachea, which contains air, has compressed slightly. The different properties of the soft tissue layers and the trachea are a result of different constraints between particles in the soft tissue model.

Figures 8C, 8D:
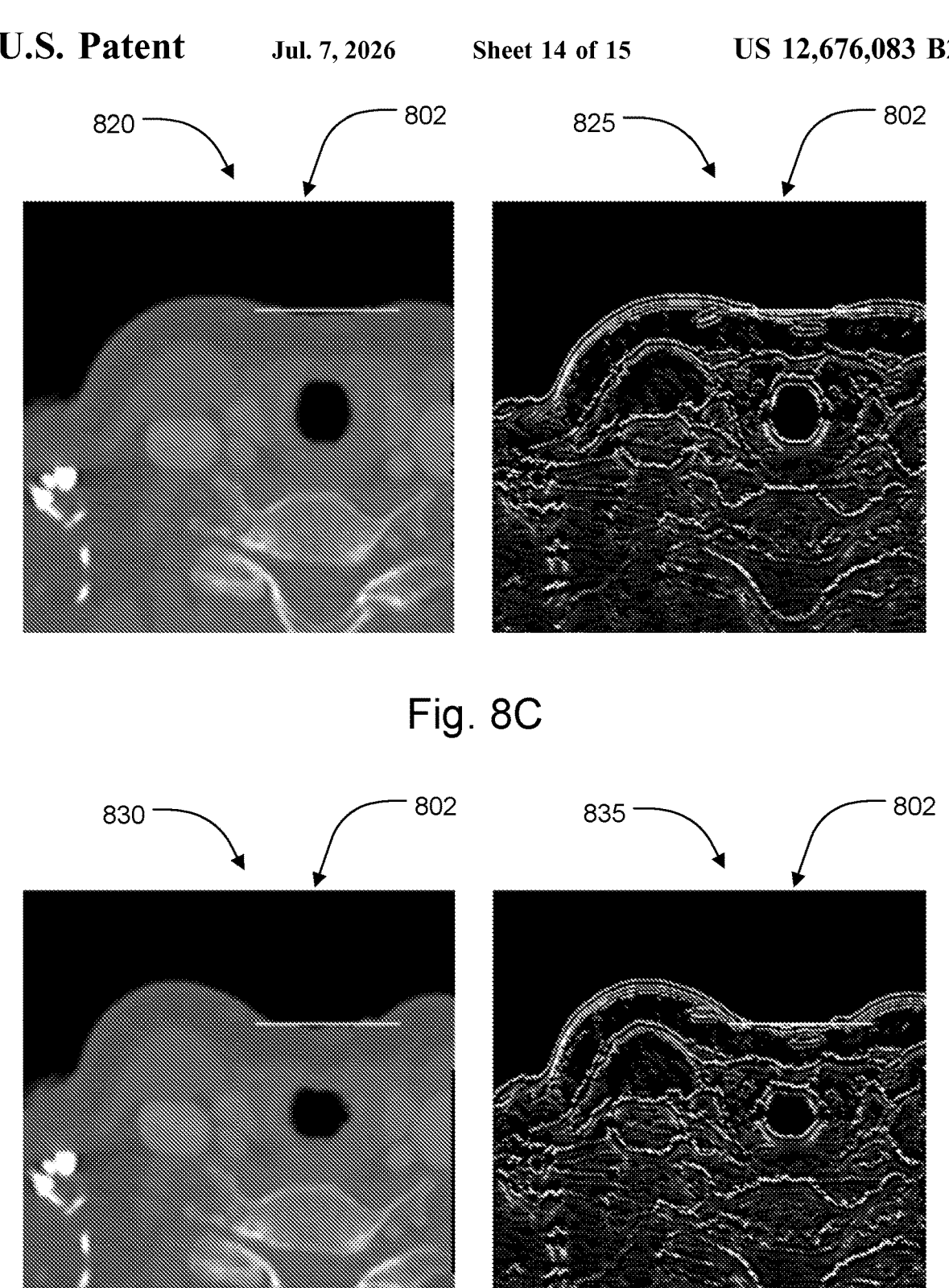

FIG. 8C shows the ultrasound probe 802 pressed against the skin with more pressure, compared to FIG. 8B, in simulated CT image 820 and simulated ultrasound image 825. The trachea has compressed more than shown in FIG. 8B while the soft tissue has not compressed. The effect of volume preservation due to the constraints used in the soft tissue regions of the soft tissue model may be seen where the skin of the virtual patient, on the left of the image, is pushed outwards by the ultrasound probe 802. The sternocleidomastoid muscle to the left of the trachea can be seen to be deformed as the tissue displaced by the probe has applied pressure.

FIG. 8D shows the ultrasound probe 802 pressed against the skin of the virtual patient with a heavy pressure in a simulated CT image 830 and a simulated ultrasound image 835. The images of FIG. 8D show the trachea has compressed further while the soft tissue has not compressed due to the different constraints used in different regions of the soft tissue model from which the simulated CT image 830 and the simulated ultrasound image 835 were generated.

Figure 9:
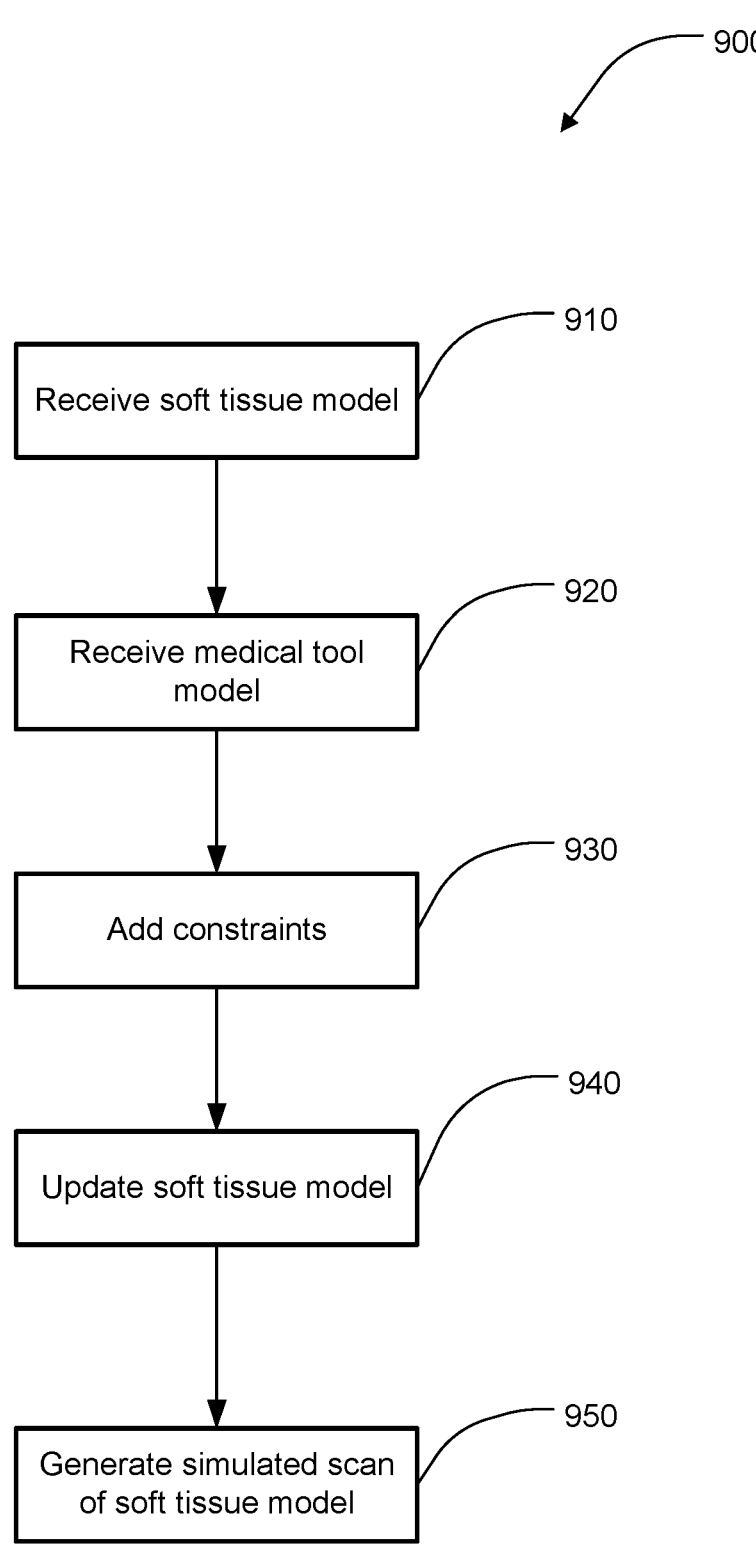
FIG. 9 illustrates a method of generating a scanned image from the dynamic virtual of FIG. 3.

A dynamic virtual ultrasound method 900 will now be described with reference to FIG. 9. The dynamic virtual ultrasound method 900 may be practiced on a computer such as the processing system 100 communicating over the network 202 and may implement the dynamic virtual ultrasound 300. The dynamic virtual ultrasound method 900 starts with a receive soft tissue model step 910 where a soft tissue model for a virtual patient is loaded to the processing system 100. The soft tissue model may be loaded from a storage device attached to the processing system 100. The soft tissue model is typically prepared before operation of the dynamic virtual ultrasound.

At a receive medical tool model step 920 one or more models of a medical tool may be loaded by the dynamic virtual ultrasound method 900. The medical tool may be selected by an operator through menu options on the dynamic virtual ultrasound. Alternatively, the medical tool may be selected by having an operator of the dynamic virtual ultrasound pick up a virtual tool in a virtual environment.

At an add constraints step 930 constraints are added between particles of the medical tool from the receive medical tool model step 920 and the particles of the soft tissue model from the receive soft tissue model step 910. The linking between the particles are described above.

At an update soft tissue model step 940 the effect of the interaction between the medical tool and the soft tissue model is determined using the constraints added in the add constraints step 930. The updated soft tissue model is determined using a position based dynamics solver as described in relation to the dynamic position based dynamics solver 320.

The last step of dynamic virtual ultrasound method 900 is a generated simulated scan step 950 where the acoustic simulator 340 described above is used to generate an image of the scanned soft tissue model. The generated image is then displayed to a user of the dynamic virtual ultrasound.

The configuration of the soft tissue model may be varied for a dynamic virtual ultrasound. For example, spacing between particles may be varied or the arrangement of the particles may be varied by using a different mesh type. For example, the mesh may be square, hexahedral, tetrahedral, or a non-uniform mesh type. A multi resolution mesh may also be used where resolution of the mesh is varied for different regions of the soft tissue model. In one example, the spacing between the particles of the soft tissue model are varied across the soft tissue model so that particles of the soft tissue model are closer together for regions where there is interaction between a medical tool and the soft tissue. Alternatively, the spacing of the particles may vary according to a region type with an air filled region having particles further apart than a less compressible region of the soft tissue model.

The dynamic virtual ultrasound may use an iterative solver for the position based dynamics solver. Performing more iterations of the position based dynamics solver may provide a more accurate solution at the cost of a longer compute time. In order to meet real-time requirements, fewer iterations can be performed at the expense of the accuracy of the physical simulation. In practical terms, so long as the simulation appears to be plausible to the user, and dynamic virtual ultrasound achieves the desired training outcomes or transfer of knowledge, then the accuracy may be considered acceptable.

The acoustic simulation, as described in relation to the acoustic simulator 340, may use stochastic ray tracing where multiple rays are traced from each transducer element. Tracing more rays may provide a more accurate image with less noise. However, in practice, the details lost by tracing fewer rays may only have a minor effect on the interpretation of ultrasound images while noise may be reduced with post processing.

The use of a position based dynamics solver in the dynamic virtual ultrasound provides advantages over other approaches to modelling deformation of soft tissue. Approaches such as Finite Element Method (FEM), Mass Spring Damper System (MSDS), or some minor variation may present challenges if used for a dynamic virtual ultrasound. For example, finite element modelling, while being accurate, is a computationally expensive approach that may be too slow for use in a real-time system. Finite element modelling and mass spring damper system approaches may also have difficulty with volume preservation used for incompressible tissue. Further, medical tools require additional constraints that may not easily be represented in a finite element model. Both finite element models and mass spring damper systems operate based on forces, solving for resulting velocities and positions of elements in the system. However, force based methods may become unstable, resulting in large forces, velocities and displacements. The use of a position based dynamics solver, such as XPBD or Small Steps for XPBD, allows the dynamic virtual ultrasound to operate in real-time with a sufficient resolution and stability to be useful as a realistic ultrasound simulation.

The use of soft tissue models generated from CT scans or MRI scans allows for a broader range of patient types to be used. The range of patients may often be limited by the difficulty in generating a new patient model. The dynamic virtual ultrasound may have new patient models developed from existing scans and may allow for a broad range of patients compared to other systems.

The interaction between particles of a medical tool and soft tissue model particles allows the soft tissue to push back on the tools. Further, the use of different constraint types allows the soft tissue model to accurately model soft tissue with different properties, such as compressible and incompressible. Different aspects of the soft tissue model may be varied to change operation of the dynamic virtual ultrasound. For example, the dynamic virtual ultrasound may vary the complexity of the soft tissue model depending on what is important for a given simulation. The soft tissue model complexity may be varied by changing the spacing between particles of the soft tissue model.

The reference in this specification to any prior publication (or information derived from the prior publication), or to any matter which is known, is not, and should not be taken as an acknowledgment or admission or any form of suggestion that the prior publication (or information derived from the prior publication) or known matter forms part of the common general knowledge in the field of endeavour to which this specification relates.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The invention claimed is:

1. A method of simulating an ultrasound scan of tissue in real-time, the method comprising:
   loading a three dimensional deformable soft tissue model of a tissue region for scanning, the deformable soft tissue model being a volumetric model simulated using soft body dynamics,
   wherein the deformable soft tissue model includes a plurality of particles and each of the plurality of particles are linked using at least one constraint,
   wherein a first particle of the plurality of particles is linked to a second particle of the plurality of particles of the deformable soft tissue model using the at least one constraint and particles in a compressible region of the deformable soft tissue model are connected to adjacent particles with distance constraints and particle in an incompressible region of the deformable soft tissue model are connected to adjacent particles with volume constraints;
   determining a three dimensional interaction between the deformable soft tissue model and at least one virtual medical tool, the at least one virtual medical tool being inserted into the tissue region;
   deforming the deformable soft tissue model according to the three dimensional interaction and properties of the deformable soft tissue model, the properties including compressible and incompressible regions of the deformable soft tissue model; and generating a simulated scan of the tissue in real-time according to a position of an ultrasound probe and the modified soft tissue model.

2. The method according to claim 1, wherein the deformable soft tissue model comprises a mesh and each of the plurality of particles are located at vertices of the mesh.

3. The method according to claim 2, wherein a voxel model overlaps the deformable soft tissue model and is used to derive continuously varying material properties of the deformable soft tissue model.

4. The method according to claim 1, wherein the at least one constraint is selected from the set consisting of a distance constraint, a volume constraint and a contact constraint.

5. The method according to claim 1, wherein a model of the virtual medical tool includes a plurality of particles and a particle of the plurality of particles is linked to a particle of the plurality of particles of the deformable soft tissue model using at least one constraint, wherein the at least one constraint is selected from the set consisting of a distance constraint, a volume constraint and a contact constraint.

6. The method according to claim 1, wherein modifying the deformable soft tissue model comprises:

locating particles of the deformable soft tissue model nearby the virtual medical tool;

attaching a plurality of particles of the deformable soft tissue model to a plurality of particles of the virtual medical tool using constraints; and determining a new location for the plurality of particles of the deformable soft tissue model and a new location for the plurality of particles of the virtual medical tool base on movement of the virtual medical tool.

7. The method according to claim 1, wherein the at least one virtual medical tool is selected from a set of virtual medical tools consisting of a hypodermic needle, a cannula, a scalpel, sutures, dressing, and forceps.

8. The method according to claim 1, wherein the modification to the deformable soft tissue model is performed by an extended position based dynamics (XPBD) solver.

9. The method according to claim 1, wherein generating the simulated scan further comprises:

forming an image slice using material properties of the virtual medical tool and the properties of the deformable soft tissue model, wherein the material properties of the virtual medical tool produce acoustic anomalies associated with the virtual medical tool.

10. A virtual ultrasound system for simulating an ultrasound scan of tissue in real-time, the system comprising:

a deformable soft tissue model of a tissue region, the deformable soft tissue model being a volumetric model simulated using soft body dynamics, wherein the deformable soft tissue model includes a plurality of particles and each of the plurality of particles are linked using at least one constraint, wherein a first particle of the plurality of particles is linked to a second particle of the plurality of particles of the deformable soft tissue model using the at least one constraint, wherein the at least one constraint is selected from the set consisting of a distance constraint, a volume constraint and a contact constraint and particles in a compressible region of the deformable soft tissue model are connected to adjacent particles with distance constraints and particle in an incompressible region of the deformable soft tissue model are connected to adjacent particles with volume constraints;

a model of at least one virtual medical tool;

a position based dynamics solver configured to determine a three dimensional interaction between the deformable soft tissue model and the model of the at least one virtual medical tool, when the at least one virtual medical tool is inserted in to the tissue region, in real-time, the position based dynamics solver also being configured to deform the deformable soft tissue model according to the three dimensional interaction and properties of the deformable soft tissue model, wherein the properties include compressible and incompressible regions of the deformable soft tissue model;

an acoustic simulator configured to generate a simulated scan of the tissue according to a position of an ultrasound probe and the modified soft tissue model; and an output device for displaying the simulated scan of the tissue.

11. The virtual ultrasound system according to claim 10, wherein the deformable soft tissue model comprises a mesh and each of the plurality of particles are located at a vertices of the mesh.

12. The virtual ultrasound system according to claim 11, wherein a voxel model overlaps the deformable soft tissue model and is used to derive continuously varying material properties of the deformable soft tissue model.

13. The virtual ultrasound system according to claim 10, wherein a model of the virtual medical tool includes a plurality of particles and a particle of the plurality of particles of the model of the virtual medical tool is linked to a particle of the plurality of particles of the deformable soft tissue model using at least one constraint, wherein the at least one constraint is selected from the set consisting of a distance constraint, a volume constraint and a contact constraint.

14. The virtual ultrasound system according to claim 10, wherein the virtual medical tool is selected from a set of medical tools consisting of a hypodermic needle, a cannula, a scalpel, sutures, dressing, and forceps.

15. The virtual ultrasound system according to claims 10, wherein the position based dynamics solver is an extended position based dynamics (XPBD) solver.

16. The virtual ultrasound system according to claim 10, wherein the acoustic simulator further comprises:

an image slice generator configured to form an image slice using material properties of the virtual medical tool and the properties of the deformable soft tissue model, wherein the material properties of the virtual medical tool produce acoustic anomalies associated with the virtual medical tool.

* * * * *